(12) United States Patent
Schuurink et al.

(10) Patent No.: US 9,234,193 B2
(45) Date of Patent: *Jan. 12, 2016

(54) PEST RESISTANT PLANTS

(75) Inventors: Robert Cornelis Schuurink, Wageningen (NL); Michael Albertus Haring, Wageningen (NL); Petronella Martina Bleeker, Wageningen (NL)

(73) Assignee: Keygene N.V., Wageningen (NL)

(*) Notice: Subject to any disclaimer, the term of this patent is extended or adjusted under 35 U.S.C. 154(b) by 0 days.

This patent is subject to a terminal disclaimer.

(21) Appl. No.: 14/122,579

(22) PCT Filed: May 31, 2012

(86) PCT No.: PCT/NL2012/050382
§ 371 (c)(1),
(2), (4) Date: Jan. 28, 2014

(87) PCT Pub. No.: WO2012/165961
PCT Pub. Date: Dec. 6, 2012

(65) Prior Publication Data
US 2014/0157456 A1    Jun. 5, 2014

Related U.S. Application Data

(60) Provisional application No. 61/607,008, filed on Mar. 6, 2012, provisional application No. 61/491,339, filed on May 31, 2011.

(51) Int. Cl.
*C12N 15/82* (2006.01)
*C12N 9/88* (2006.01)
(Continued)

(52) U.S. Cl.
CPC .. *C12N 9/88* (2013.01); *A01H 1/04* (2013.01); *C12N 15/8239* (2013.01);
(Continued)

(58) Field of Classification Search
CPC ................................ C12N 15/8286; C12N 9/88
See application file for complete search history.

(56) References Cited

U.S. PATENT DOCUMENTS

2010/0138954 A1 * 6/2010 Sallaud et al. ............... 800/278

FOREIGN PATENT DOCUMENTS

| EP | 0 583 774 B1 | 2/1994 |
|----|---|---|
| ES | 2341085 A1 | 6/2010 |

(Continued)

OTHER PUBLICATIONS

Gonzales-Vigil E., et al., 2012. "Evolution of TPS20-related terpene synthases influences chemical diversity in the glandular trichomes of the wild tomato relative Solanum habrochaites." Plant J. 71:921-935.*

(Continued)

*Primary Examiner* — Amjad Abraham
*Assistant Examiner* — Weihua Weihua
(74) *Attorney, Agent, or Firm* — Foley & Lardner LLP; Sunit Talapatra

(57) ABSTRACT

An isolated nucleic acid molecule encoding a 7-epizingiberene synthase, a chimeric gene comprising the nucleic acid molecule, vectors comprising the same, as well as isolated 7-epizingiberene synthase proteins themselves, are provided. In addition, transgenic plants and plant cells comprising a gene encoding a 7-epizingiberene synthase, optionally integrated in its genome, and methods for making such plants and cells, are provided. Especially Solanaceae plants and plant parts (seeds, fruit, leaves, etc.) with enhanced insect pest resistance are provided.

23 Claims, 22 Drawing Sheets

(51) Int. Cl.
*A01H 1/04* (2006.01)
*C12P 5/00* (2006.01)
(52) U.S. Cl.
CPC ....... *C12N 15/8243* (2013.01); *C12N 15/8286* (2013.01); *C12P 5/007* (2013.01); *C12Y 402/00* (2013.01); *C12Y 402/03053* (2013.01); *C12Y 402/03054* (2013.01); *C12Y 402/03082* (2013.01)

(56) References Cited

FOREIGN PATENT DOCUMENTS

| FR | WO2008142318 | * | 11/2008 | ............... C12N 9/10 |
|---|---|---|---|---|
| WO | WO-2008/142318 A2 | | 11/2008 | |
| WO | WO-2010/099985 A2 | | 9/2010 | |
| WO | WO-2013/006190 A1 | | 1/2013 | |

OTHER PUBLICATIONS

Evertsz, E. M., et al. "Research Report Hybridization Cross-Reactivity within Homologous Gene Families on Glass cDNA Microarrays." Biotechniques 31.5 (2001): 1182-1192.*
Bleeker, Petra M., et al. "Tomato-produced 7-epizingiberene and R-curcumene act as repellents to whiteflies." Phytochemistry 72.1 (2011): 68-73.*
Evertsz, et al. "Hybridization Cross-Reactivity within Homologous Gene Families on Glass cDNA Microarrays", Drug Discovery and Genomic Technologies (2001), vol. 31, No. 5, pp. 1182-1192.
GenBank protein ID # AFJ67794—"Zingiberene synthase [Solanum habrochaites]" www.ncbi.nlm.nih.gov/protein/AFJ67794—Online Jan. 30, 2015.
GenBank protein ID # AHF95242—"cis-prenyltransferase [Solanum habrochaites]", www.ncbi.nlm.nih.gov/protein/AHF95242—Online—Jan. 30, 2015.
Gonzales-Vigil, et al. "Evolution of TPS20-related terpene synthases influences chemical diversity in the glandular trichomes of the wild tomato relative Solanum habrochaites", The Plant Journal (2012), vol. 71, pp. 921-935.
Kang, et al. "Determination of Residues Responsible for Substrate and Product Specificity of Solanum habrochaites Short-Chain cis-Prenyltransferases", Plant Physiology (Jan. 2014), vol. 164, pp. 80-91.
Antonious, "Production and Quantification of Methyl Ketones in Wild Tomato Accessions", Journal of Environmental Science and Health, Part B: Pesticides, Food Contaminants, and Agricultural Wastes, 2001, vol. 36, No. 6, pp. 835-848.
Antonious, et al., "Natural Products: Seasonal Variation in Trichome Counts and Contents in Lycopersicum hirsutum f. glabratum", J. Environ Sci Health Part B, 2005, vol. 40, pp. 619-631.
Antonious, G et al., "Zingiberene and Curcumene in Wild Tomato," Journal of Environmental Science and Health—Part B—Pesticides, Food, Contaminants, and Agricultural Wastes, vol. B38, 2003, No. 4, pp. 489-500.
Bruce, et al., "Insect host location: a volatile situation", TRENDS in Plant Science, Jun. 2005, vol. 10, No. 6, pp. 269-274.
De Azavedo et al., "International Journal of Plant Breeding", Euphytica, 2003, vol. 134, No. 3, pp. 247-351.
Freitas, et al., "Inheritance of foliar zingiberene contents and their relationship to trichome densities and whitefly resistance in tomatoes", Euphytica, 2002, vol. 127, pp. 275-287.
Heinz, et al., "Variation in Trichome-Based Resistance to Bemisia argentifolii (Homoptera: Aleyrodidae) Oviposition on Tomato", J. Econ Entomol, (1995), vol. 88, pp. 1494-1502.
Iijima, et al., "The Biochemical and Molecular Basis for the Divergent Patterns in the Biosynthesis of Terpenes and Phenylpropenes in the Peltate Glands of Three Cultivars of Basil", Plant Physiology, 2004, vol. 136, No. 3, pp. 3724-3736.
Kauffman, et al., "Inhibition of Campoletis sonorensis Parasitism of Heliothis zea and of Parasitoid Development by 2-Tridecanone-Mediated Insect Resistance of Wild Tomato", Journal of Chemical Ecology, 1989, vol. 15, No. 6, pp. 1919-1930.
Pushkar, et al. "Alternative medicine: Herbal drug and their critical appraisal", Jucker, E. Progress in Drug Research, 2001, vol. 57.
Bleeker, P. et al., "Tomato-produced 7-epizingiberene and R-curcumene act as repellents to whiteflies," Phytochemistry, vol. 72, No. 1, Jan. 1, 2011, pp. 68-73.
Database EMBL [Online], "Solanum habrochaites isolate LA2167 zingiberene synthase mRNA, complete cds.", XP002682420, retrieved from EBI accession No. EMBL:JN990661, Database accession No. JN990661 sequence, 2 pgs.
Davidovich-Rikanati, R. et al, "Overexpression of the lemon basil [alpha]-zingiberene synthase gene increases both mono—and sesquiterpene contents in tomato fruit," The Plant Journal, vol. 56, No. 2, Oct. 1, 2008, pp. 228-238.
International Search Report mailed Sep. 6, 2012 in International Appln. No. PCT/NL2012/050382, 5 pgs.

* cited by examiner

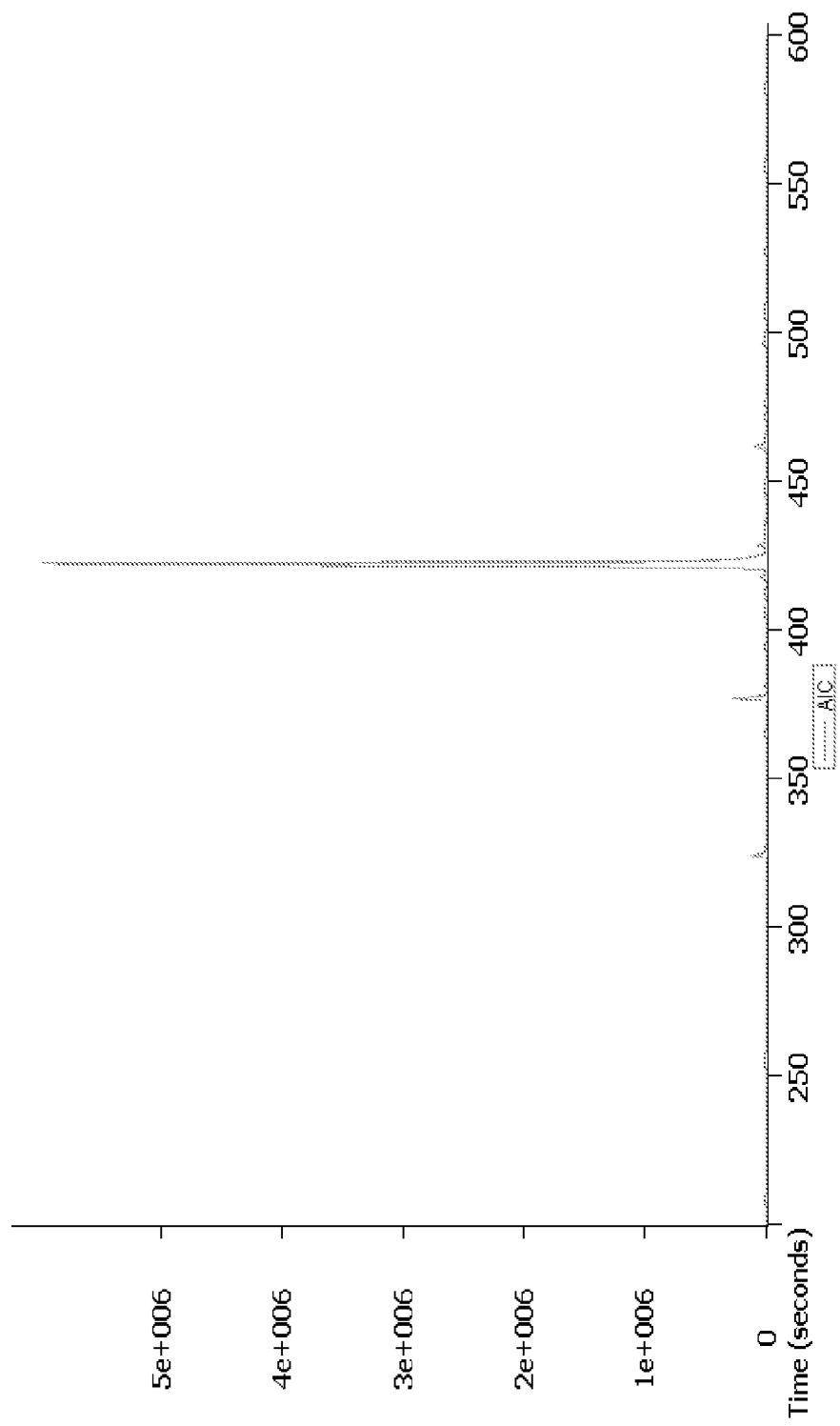

PEST RESISTANT PLANTS

CROSS-REFERENCE TO RELATED APPLICATION

This application is the National Phase of International Patent Application No. PCT/NL2012/050382, filed May 31, 2012, published in English as WO 2012/165961, which claims priority to U.S. Provisional Application Nos. 61/491,339, filed May 31, 2011 and 61/607,008, filed Mar. 6, 2012. The contents of these applications are herein incorporated by reference in their entirety.

FIELD OF THE INVENTION

The present invention relates to an isolated nucleic acid molecule encoding a 7-epizingiberene synthase, a chimeric gene comprising said nucleic acid molecule, vectors comprising the same, host cells comprising such vector, as well as isolated zingiberene synthase proteins themselves. The present invention further provides a method for preparing 7-epizingiberene using such nucleic acid molecule. In addition, transgenic plants and plant cells comprising a gene encoding such zingiberene synthase, optionally integrated in its genome, and methods for making such plants and cells, are provided. Especially Solanaceae plants and plant parts (seeds, fruit, leaves, etc.) with enhanced insect pest resistance are provided.

BACKGROUND OF THE INVENTION

Some common insect pests of agronomically important crop plants such as tomatoes include the South American Tomato Leaf Miner (*Tuta absoluta*), stink bugs, cutworms, hornworms, aphids, cabbage loopers, whiteflies (*Bemisia* and *Trialeurodes*), fruitworms, flea beetles, spider mites such as *Tetranychus urticae* (the glass house red spider mite), *Panonychus ulmi* (fruit tree red spider mite) and *Panonychus citri* (citrus red mite), insects of the order Diptera, and Colorado potato beetles (*Leptinotarsa decemlineata*).

For example, whiteflies of the genera *Bemisia* (sweet potato whitefly) and *Trialeurodes* (greenhouse whitefly) are major pests of crop plants throughout the world, causing economic losses especially due to the transmission of plant viruses during feeding (i.e. they act as 'virus vectors'). *Bemisia tabaci* is capable of transmitting more than 60 different members of the Geminiviridae, many of which belong to the Begomoviruses such as African cassava mosaic virus (ACMV), Bean golden mosaic virus (BGMV), Bean dwarf mosaic virus, Tomato yellow leaf curl virus (TYLCV), Tomato mottle virus (ToMoV), and others, plus a number of criniviruses. Both tropical and temperate crops are affected, such as tomatoes, beans, cucurbits, potatoes, cotton, cassava and sweet potatoes.

To date, the main control strategy for insect pests is the application of insecticides, aimed at killing adults, juveniles and eggs. Besides the substantial costs of insecticide application this practice has a severe environmental impact. Moreover, many insect pests are difficult to control with insecticides due to emerging resistance to the active ingredients.

In order to reduce insecticide application, there is a need for new ways of controlling crop damage and losses due to plant insect pests, both in field-grown and greenhouse-grown crops. From literature it is known that volatile components can directly influence insect behaviour (e.g. Bruce et al., 2005, Trends Plant Sci. 10: 269-74). One way to control virus transmission by plant insect pests is by identifying insect repellents, which can be applied on or near the crop plants or can be produced in the crop.

EP 0 583 774 describes the use of vegetable oil to reduce phytotoxicity of foliar insect control agents, whereby any type of insect control agent may be used.

Glandular trichomes are prominent on foliage and stems of the genus *Lycopersicon* (now classified as *Solanum*) and have been shown to produce a large number of secondary compounds, such as mono- and sesquiterpene hydrocarbons, sesquiterpene acids, methylketones and sugar esters. Several studies have tried to correlate the density of glandular trichomes with resistance against plant pests, such as maize earworm (*Heliothis zea*) or Colorado potato beetle (Kauffman and Kennedy, 1989, J Chem Ecol 15, 1919-1930; Antonious, 2001, J Environ Sci Health B 36, 835-848 and Antonious et al. 2005, J Environ Sci Health B 40: 619-631). Also the methylketones 2-undecanone and 2-tridecanone, stored in the glandular trichomes of *L. hirsutum f. glabratum* (renamed to *S. habrochaites*) were shown to exhibit a toxic effect against fourth instar larvae of Colorado potato beetle and adult whiteflies *B. tabaci*, respectively (Antonious et al. 2005, J Environ Sci Health B 40: 619-631).

Antonious and Kochhar (J Environm Science and Health B, 2003, B38: 489-500) extracted and quantified zingiberene and curcumene from wild tomato accessions with the goal of selecting wild tomato accessions that can be used for the production of sesquiterpene hydrocarbons for natural insecticide production. However, whether such compounds are able to be used as whitefly repellents or attractants was not disclosed. It is mentioned that zingiberene has been associated with Colorado beetle resistance and beet armyworm resistance, while curcumene has been associated with insecticidal effects. The wild tomato species *L. hirsutum f. typicum* (*S. habrochaites*) is mentioned to be resistant to *B. argentifolii* (now named *B. tabaci*) (Heinz et al. 1995, 88:1494-1502), but trichome based plant resistance could, of course, have various causes and from this paper one cannot make inferences regarding the presence or identity of compounds which have properties for attracting or repelling whiteflies.

Freitas et al. (Euphytica 2002, 127: 275-287) studied the genetic inheritance of the genes for the production of both the sesquiterpene zingiberene and glandular trichome types I, IV, VI and VII in interspecific crosses between *L. esculentum* (*S. lycopersicum*; cultivated tomato, no zingiberene) and wild *L. hirsutum* var. *hirsutum* (*S. habrochaites*; high in zingiberene). Zingiberene content in $F_2$ plants contributed to *B. argentifolii* (*B. tabaci*) resistance by correlation and it was suggested to breed plants with simultaneously high levels of zingiberene, 2-tridecanone and/or acylsugars to contribute to higher levels of whitefly resistance.

ES 2341085 discloses exogenous application of alpha-zingiberene as a repellent and insecticide against *T. absoluta* and other insects that affect tomato crops. Alpha-zingiberene may be applied in its pure form, or in its natural form through the use of essential oils containing the molecule in appropriate concentrations.

De Azavedo et al., Euphytica 2003, 134, 247-351 describe the effect of endogenous zingiberene mediated resistance to *T. absoluta*.

According to Pushkar, N. K. and Balawant, S. J. (2001) "Alternative medicine: Herbal drugs and their critical appraisal" in Jucker, E. Progress in Drug Research, Vol. 57, ginger essential oil contains alpha-zingiberene, but not 7-epizingiberene (Table 4, page 46).

Bleeker et al., Phytochemistry 2011, 72(1):68-73 disclose that 7-epizingiberene and R-curcumene, both purified from

*Solanum habrochaites* (PI127826), act as repellent to *Bemisia tabaci* whiteflies, while stereoisomers alpha-zingiberene and S-curcumene from *Zingiber officinalis* oil (ginger oil) do not. Bio-assays showed that a cultivated tomato could be made less attractive to *B. tabaci* than its neighbouring siblings by the addition of the tomato stereoisomer 7-epizingiberene or its derivative R-curcumene (abstract).

Davidovich-Rikanati et al., The Plant Journal 2008, 56(2): 228-238 disclose the transformation of tomato plants with a construct harbouring the alpha-zingiberene synthase of lemon basil (*Ocimum basilicum* L.) coupled to the fruit ripening-specific tomato polygalacturonase promoter (PG). The overexpression of alpha-zingiberene synthase results in the production of alpha-zingiberene by the transgenic tomatoes. It is further described that alpha-zingiberene is a major leaf oil sesquiterpene in *Solanum hirsutum*, and this trait has been associated with resistance to *B. tabaci*.

Iijima et al., Plant Physiology 2004, 136(3):3724-3736 disclose the isolation and expression in *E. coli* of an alpha-zingiberene synthase of sweet basil.

Although several methods exist for combating plant insect pests, there is still a need for adequate protection against insect pests such as, for example, *B. tabaci*.

SUMMARY OF THE INVENTION

The present inventors have now identified a gene encoding a 7-epizingiberene synthase protein from *Solanum habrochaites* (ShZIS).

Thus, in a first aspect, the present invention provides an isolated protein comprising the amino acid sequence of SEQ ID NO: 1 or an amino acid sequence comprising at least 92% amino acid sequence identity to the amino acid sequence of SEQ ID NO:1 over the entire length. The present invention further provides an isolated, synthetic or recombinant nucleic acid sequence selected from the group comprising: a) a nucleic acid sequence of SEQ ID NO: 2; b) a nucleic acid sequence that encodes a polypeptide comprising an amino acid sequence of SEQ ID NO: 1; c) a nucleic acid sequence that is at least 92% identical to the nucleic acid sequences of (a) or (b), and encodes a 7-epizingiberene synthase; d) a nucleic acid sequence encoding a polypeptide comprising an amino acid sequence of SEQ ID NO:1 wherein at least one amino acid is substituted, deleted, inserted or added and wherein the polypeptide is functionally equivalent to the polypeptide consisting of the amino acid sequence of SEQ ID NO:1; and e) a nucleic acid sequence that hybridizes under stringent conditions to the nucleic acid sequences of (a), (b), or (c), and encodes a 7-epizingiberene synthase; a chimeric gene comprising a promoter, optionally active in plant cells, operably linked to such nucleic acid molecule, and, optionally, further operably linked to a 3' untranslated nucleic acid molecule, as well as a vector comprising such chimeric gene. A host cell comprising such vector is also included in the present invention.

The present invention is also directed to a method for preparing 7-epizingiberene and/or R-curcumene comprising the steps of: a) transforming a host cell with the nucleic acid molecule, a chimeric gene or a vector according to the present invention; b) culturing said host cell under conditions permitting production of 7-epizingiberene; c) optionally, isolating the 7-epizingiberene produced in step b); and d) optionally, dehydrogenating said 7-epizingiberene to produce R-curcumene.

In another aspect, the present invention is concerned with a method for producing 7-epizingiberene from zFPP in a host cell, comprising: a) introducing into said host cell a first nucleic acid sequence encoding a zFPS as shown in SEQ ID NO:6 or an amino acid sequence comprising at least 80% amino acid sequence identity to the amino acid sequence of SEQ ID NO:6 over the entire length, and a second nucleic acid sequence encoding a 7-epizingiberene synthase comprising the amino acid sequence of SEQ ID NO: 1 or an amino acid sequence comprising at least 92% amino acid sequence identity to the amino acid sequence of SEQ ID NO:1; b) culturing the transformed host cell in suitable conditions for the expression of said first and said second nucleic acid sequences; and, c) optionally, collecting the zFPP and/or the 7-epizingiberene contained in said host cell and/or in the culture medium.

In a further aspect, the present invention pertains to a transgenic plant, plant cell, seed or fruit, comprising a nucleotide sequence encoding the amino acid sequence of SEQ ID NO:1 or an amino acid sequence comprising at least 92% amino acid sequence identity to the amino acid sequence of SEQ ID NO:1 over the entire length.

In yet another aspect, the present invention relates to a *Solanum lycopersicum* plant, plant cell, seed or fruit comprising a nucleic acid sequence encoding the amino acid sequence of SEQ ID NO:1 or an amino acid sequence comprising at least 92% amino acid sequence identity to the amino acid sequence of SEQ ID NO:1 over the entire length. Preferably, said *Solanum lycopersicum* plant, plant cell, seed or fruit further comprises a nucleic acid sequence encoding a Z,Z-farnesyl-diphosphate synthase (herein also referred to as a "zFPP" or Z,Z-FPP).

In a further aspect, the present invention provides a method for producing a transgenic plant having enhanced insect pest resistance compared to a non-transgenic control plant, said method comprising the steps of: (a) transforming a plant or plant cell with a nucleic acid molecule encoding the amino acid sequence of SEQ ID NO: 1 or an amino acid sequence comprising at least 92% amino acid sequence identity to the amino acid sequence of SEQ ID NO:1 over the entire length, operably linked to a promoter active in plant cells, and (b) regenerating a plant. Said nucleic acid molecule may be integrated into the genome of said plant. Said method may further comprise the step of (c) screening the regenerated plant, or a plant derived therefrom by selfing or crossing, for resistance to one or more insect pests and identifying a plant comprising enhanced resistance to one or more of said insect pests. The promoter may be an insect pest inducible promoter. The plant may belong to the family Solanaceae. The plant may be of the genus *Solanum*.

In an embodiment, the method further comprises the step of transforming the plant or plant cell with a nucleic acid molecule encoding the amino acid sequence of SEQ ID NO:5 or an amino acid sequence comprising at least 80% amino acid sequence identity to the amino acid sequence of SEQ ID NO:6, preferably over the entire length, operably linked to a promoter active in plant cells.

In a further aspect, the present invention relates to the use of a nucleic acid molecule encoding the amino acid sequence of SEQ ID NO:1 or an amino acid sequence comprising at least 92% amino acid sequence identity to the amino acid sequence of SEQ ID NO:1 over the entire length for the generation of insect pest resistant plants.

In a final aspect, the present invention is concerned with a method for identifying a genomic polymorphism between *Solanum habrochaites* and species of the *Solanum* type that are sexually compatible with *Solanum habrochaites* comprising detecting a genomic polymorphism with molecular markers comprising all or part of the gene encoding the amino acid sequence of SEQ ID NO:1 or an amino acid sequence having at least 92% sequence identity with the amino acid sequence of SEQ ID NO:1 so as to control the introgression of the corresponding gene in said species.

General Definitions

The term "nucleic acid molecule" (or "nucleic acid sequence") refers to a DNA or RNA molecule in single or double stranded form, particularly a DNA encoding a protein according to the invention. An "isolated nucleic acid sequence" refers to a nucleic acid sequence which is no longer in the natural environment from which it was isolated, e.g. the nucleic acid sequence in a bacterial host cell or in the plant nuclear or plastid genome.

The terms "protein" or "polypeptide" are used interchangeably and refer to molecules consisting of a chain of amino acids, without reference to a specific mode of action, size, 3 dimensional structure or origin. An "isolated protein" is used to refer to a protein which is no longer in its natural environment, for example in vitro or in a recombinant bacterial or plant host cell.

The term "7-epizingiberene synthase" or "7-epizingiberene synthase protein" as used herein denotes a 7-epizingiberene synthase protein, i.e., the protein of the invention is capable of converting Z,Z-farnesyl-diphosphate into 7-epizingiberene.

"Functional", in relation to 7-epizingiberene synthase proteins (or variants, such as orthologs or mutants, and fragments), refers to the capability to provide insect pest resistance by modifying the expression level of the 7-epizingiberene synthase-encoding gene in a plant.

The term "gene" means a DNA sequence comprising a region (transcribed region), which is transcribed into a RNA molecule (e.g. a mRNA) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA), introns, and a 3' non-translated sequence comprising e.g. transcription termination sites.

A "chimeric gene" (or recombinant gene) refers to any gene, which is not normally found in nature in a species, in particular a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense (reverse complement of the sense strand) or inverted repeat sequence (sense and antisense, whereby the RNA transcript forms double stranded RNA upon transcription).

A "3' UTR" or "3' non-translated sequence" (also often referred to as 3' untranslated region, or 3'end) refers to the nucleic acid sequence found downstream of the coding sequence of a gene, which comprises for example a transcription termination site and (in most, but not all eukaryotic mRNAs) a polyadenylation signal (such as e.g. AAUAAA or variants thereof). After termination of transcription, the mRNA transcript may be cleaved downstream of the polyadenylation signal and a poly(A) tail may be added, which is involved in the transport of the mRNA to the cytoplasm (where translation takes place).

"Expression of a gene" refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment) or which is active itself (e.g. in posttranscriptional gene silencing or RNAi). An active protein in certain embodiments refers to a protein being constitutively active. The coding sequence is preferably in sense-orientation and encodes a desired, biologically active protein or peptide, or an active peptide fragment. In gene silencing approaches, the DNA sequence is preferably present in the form of an antisense DNA or an inverted repeat DNA, comprising a short sequence of the target gene in antisense or in sense and antisense orientation. "Ectopic expression" refers to expression in a tissue in which the gene is normally not expressed.

A "transcription regulatory sequence" is herein defined as a nucleic acid sequence that is capable of regulating the rate of transcription of a (coding) sequence operably linked to the transcription regulatory sequence. A transcription regulatory sequence as herein defined will thus comprise all of the sequence elements necessary for initiation of transcription (promoter elements), for maintaining and for regulating transcription, including e.g. attenuators or enhancers. Although mostly the upstream (5') transcription regulatory sequences of a coding sequence are referred to, regulatory sequences found downstream (3') of a coding sequence are also encompassed by this definition.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically (e.g. by external application of certain compounds) or developmentally regulated. A "tissue specific" promoter is only active in specific types of tissues or cells. A "promoter active in plants or plant cells" refers to the general capability of the promoter to drive transcription within a plant or plant cell. It does not make any implications about the spatiotemporal activity of the promoter.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous.

The terms "target peptide" refers to amino acid sequences which target a protein, or protein fragment, to intracellular organelles such as plastids, preferably chloroplasts, mitochondria, or to the extracellular space or apoplast (secretion signal peptide). A nucleic acid sequence encoding a target peptide may be fused (in frame) to the nucleic acid sequence encoding the amino terminal end (N-terminal end) of the protein or protein fragment, or may be used to replace a native targeting peptide.

A "nucleic acid construct" or "vector" is herein understood to mean a man-made nucleic acid molecule resulting from the use of recombinant DNA technology and which is used to deliver exogenous DNA into a host cell. The vector backbone may for example be a binary or superbinary vector (see e.g. U.S. Pat. No. 5,591,616, US 2002138879 and WO95/06722), a co-integrate vector or a T-DNA vector, as known in the art and as described elsewhere herein, into which a chimeric gene is integrated or, if a suitable transcription regulatory sequence is already present, only a desired nucleic acid sequence (e.g. a coding sequence, an antisense or an inverted repeat sequence) is integrated downstream of the transcription regulatory sequence. Vectors usually comprise further genetic elements to facilitate their use in molecular cloning, such as e.g. selectable markers, multiple cloning sites and the like (see below).

"Stringent hybridisation conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point ($T_m$) for the specific sequences at a defined ionic strength and pH. The $T_m$ is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001).

"Sequence identity" and "sequence similarity" can be determined by alignment of two peptide or two nucleotide sequences using global or local alignment algorithms. Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length, maximizing the number of matches and minimises the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or EmbossWin version 2.10.0 (using the program "needle"). Alternatively percent similarity or identity may be determined by searching against databases, using algorithms such as FASTA, BLAST, etc. Preferably, the sequence identity refers to the sequence identity over the entire length of the sequence.

A "host cell" or a "recombinant host cell" or "transformed cell" are terms referring to a new individual cell (or organism) arising as a result of at least one nucleic acid molecule, especially comprising a chimeric gene encoding a desired protein or a nucleic acid sequence which upon transcription yields an antisense RNA or an inverted repeat RNA (or hairpin RNA) for silencing of a target gene/gene family, having been introduced into said cell. The host cell is preferably a plant cell or a bacterial cell. The host cell may contain the nucleic acid construct as an extra-chromosomally (episomal) replicating molecule, or more preferably, comprises the chimeric gene integrated in the nuclear or plastid genome of the host cell. Throughout the text the term "host" may also refer to the host plant species which a pathogen is able to invade or infect, but this will be clear from the context. Plant species are classified as "host" or "non-host" species in relation to a pathogen. "Non-host" species are completely immune to pathogen infection of all races or strains of a pathogen, even under optimum conditions for disease development. The "host" species are also referred to as the "host range" of a pathogen and are immune to certain (but not all) races of a pathogen.

The term "selectable marker" is a term familiar to one of ordinary skill in the art and is used herein to describe any genetic entity which, when expressed, can be used to select for a cell or cells containing the selectable marker. Selectable marker gene products confer for example antibiotic resistance, or more preferably, herbicide resistance or another selectable trait such as a phenotypic trait (e.g. a change in pigmentation) or nutritional requirements. The term "reporter" is mainly used to refer to visible markers, such as green fluorescent protein (GFP), eGFP, luciferase, GUS and the like.

The terms "pests" and "pest" as used herein refer to "plant insect pests" or "plant pests" or "insect pests" or "plant pest species". Such plant insect pests include insect species that cause infestation and damage on crop and/or ornamental plants (hosts plant species), by infestation of the plants or plant parts. An "infestation" is the presence of a large number of pest organisms in an area (e.g. a field or glasshouse), on the surface of a host plant or on anything that might contact a host plant, or in the soil. Plant insect pests include sap-sucking insect pests (see below), but also other insect pests, such as thrips, cicada, and leaf-hoppers. The term "insect pests" as used herein includes any herbivorous Arthropods such as mites (e.g. spider mites and others).

"Sap-sucking insect pests" include plant pests of the suborder Sternorrhyncha (of the order Hemiptera, of the class Insecta), i.e. insect pests which include psyllids, whiteflies, aphids, mealybugs and scale insects and share a common property, namely the utilization of plant sap as their food source.

"Aphids" include herein plant insect pests of the family Aphididae, such as *Aphis gossypii, A. fabae, A. glycines, A. nerii, A. nasturtii, Myzus persicae, M. cerasi, M. ornatus, Nasonovia* (e.g. *N. ribisnigri*), *Macrosiphum, Brevicoryne* and others.

"Insect vectors" are insects that are capable of carrying and transmitting viruses, bacteria, plasmodia etc. to plants.

"Whitefly" or "whiteflies" refer to species of the genus *Bemisia*, especially *B. tabaci* and *B. argentifolii* (also known as biotype B of *B. tabaci*), and/or species of the genus *Trialeurodes*, especially *T. vaporariorum* (greenhouse whitefly) and *T. abutinolea* (banded winged whitefly). Included herein are all biotypes, such as biotype Q and B of *B. tabaci*, as well as any developmental stage, such as eggs, larvae, and adults.

Throughout the application, reference is made to "7-epizingiberene". In this respect, it is important to note that 7-epizingiberene is a diastereoisomer of alpha-zingiberene (Breeden and Coates, 1994, Tetrahedron, 50 (38), 11123-

11132). The two molecules differ in the stereochemical configuration of one hydrogen and one methyl group:

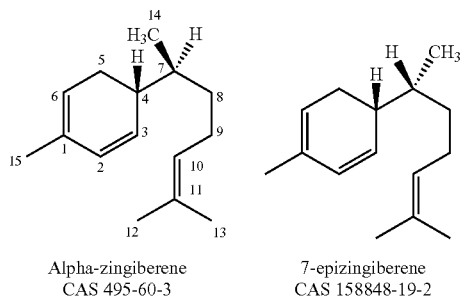

Alpha-zingiberene
CAS 495-60-3

7-epizingiberene
CAS 158848-19-2

When exposed to air, isolated 7-epizingiberene can spontaneously convert to R-curcumene. This was previously observed by Bleeker et al. (Phytochemistry. 2011 January; 72(1):68-73).

"Solanaceae" refers herein to plant genera, species, and varieties thereof, belonging to the family Solanaceae. These include species belonging to the genus *Solanum* (including *Solanum lycopersicum*, which used to be known as *Lycopersicon esculentum*), *Nicotiana, Capsicum, Petunia* and other genera.

The term "ortholog" of a gene or protein refers herein to the homologous gene or protein found in another species, which has the same function as the gene or protein, but (usually) diverged in sequence from the time point on when the species harbouring the genes diverged (i.e. the genes evolved from a common ancestor by speciation). Orthologs of the gene encoding *Solanum habrochaites* zingiberene synthase of the invention may thus be identified in other plant species based on both sequence comparisons (e.g. based on percentages sequence identity over the entire sequence or over specific domains) and functional analysis.

The terms "homologous" and "heterologous" refer to the relationship between a nucleic acid or amino acid sequence and its host cell or organism, especially in the context of transgenic organisms. A homologous sequence is thus naturally found in the host species (e.g. a tomato plant transformed with a tomato gene), while a heterologous sequence is not naturally found in the host cell (e.g. a tomato plant transformed with a sequence from potato plants). Depending on the context, the term "homolog" or "homologous" may alternatively refer to sequences which are descendent from a common ancestral sequence (e.g. they may be orthologs).

As used herein, the term "plant" includes plant cells, plant tissues or organs, plant protoplasts, plant cell tissue cultures from which plants can be regenerated, plant calli, plant cell clumps, and plant cells that are intact in plants, or parts of plants, such as embryos, pollen, ovules, fruit (e.g. harvested tomatoes), flowers, leaves, seeds, roots, root tips and the like.

In this document and in its claims, the verb "to comprise" and its conjugations is used in its non-limiting sense to mean that items following the word are included, but items not specifically mentioned are not excluded. It also encompasses the more limiting verb "to consist of". In addition, reference to an element by the indefinite article "a" or "an" does not exclude the possibility that more than one of the element is present, unless the context clearly requires that there be one and only one of the elements. The indefinite article "a" or "an" thus usually means "at least one". It is further understood that, when referring to "sequences" herein, generally the actual physical molecules with a certain sequence of subunits (e.g. amino acids) are referred to.

DETAILED DESCRIPTION OF THE INVENTION

Proteins and Nucleic Acid Sequences

The 7-epizingiberene synthase protein of the present invention has 91% sequence identity over the entire length with a protein having GenBank entry ACJ38409.1 (710 out of 777 amino acids identical), said protein being denoted as a santalene and bergamotene synthase from *Solanum habrochaites*. Said protein is known to produce (+)-alpha-santalene, (−)-endo-alpha-bergomotene en (+)-endo-beta-bergamotene (Sallaud et al., Plant Cell, vol. 21(1), 301-317, 2009 and US 2010-0138954).

In one embodiment of the invention nucleic acid sequences and amino acid sequences of 7-epizingiberene synthase proteins are provided (including orthologs), as well as methods for isolating or identifying orthologs of 7-epizingiberene synthase proteins in other plant species, such as other Solanaceae. 7-epizingiberene synthase proteins and functional fragments and variants thereof, as referred to herein, are capable of producing 7-epizingiberene starting from Z,Z-farnesyldiphosphate ("zFPP"). Thus, such proteins, as well as functional fragments and variants thereof, have 7-epizingiberene synthase activity.

In one embodiment 7-epizingiberene synthase proteins are provided. "7-epizingiberene synthase proteins" comprise the protein depicted in SEQ ID NO:1, as well as fragments and variants thereof. Variants of 7-epizingiberene synthase include, for example, proteins having at least 92%, 92.5%, 93%, 93.5%, 94%, 94.5%, 95%, 95.5%, 96%, 96.5%, 97%, 97.5%, 98%, 98.5%, 99%, 99.5% or more, such as 100%, amino acid sequence identity over the entire length to SEQ ID NO:1. Amino acid sequence identity is determined by pairwise alignment using the Needleman and Wunsch algorithm and GAP default parameters as defined above. Variants also include proteins having 7-epizingiberene activity, which have been derived, by way of one or more amino acid substitutions, deletions or insertions, from the polypeptide having the amino acid sequence of SEQ ID NO:1. Preferably, such proteins comprise from 1, 2, 3, 4, 5, 6, 7, 8, 9, 10 or more up to about 100, 90, 80, 70, 60, 50, 45, 40, 35, 30, 25, 20, 15 amino acid substitutions, deletions or insertions. For example, and without limitation, the following amino acids may be substituted: R10, P22, V42, K60, S90, N159, F190, I200, V298, A304, I310, V498, M504, S609, I626, F646. For example, and without limitation, the following substitutions may be introduced: R10Q, P22T, V42L, K60N, S90T, N159S, F190V, I200M, V298A, A304V, I310M, V498M, M504I, S609T, I626L, F646C.

Variants of 7-epizingiberene synthase can be obtained from various sources, such as from other plant species (especially other species of Solanaceae) or other varieties, or they can be made by de novo synthesis, mutagenesis and the like. The 7-epizingiberene synthase proteins according to the invention may thus be isolated from natural sources, synthesized de novo by chemical synthesis (using e.g. a peptide synthesizer such as supplied by Applied Biosystems) or produced by recombinant host cells by expressing the nucleic acid sequence encoding the 7-epizingiberene synthase protein, fragment or variant. Variants and fragments are preferably functional, i.e., have 7-epizingiberene synthase activity. When the 7-epizingiberene synthase protein of the present invention is not preceded by a targeting sequence as described below, the 7-epizingiberene synthase protein comprising the amino acid sequence of SEQ ID NO:1 or a variant thereof as defined herein will be preceded by a methionine residue, and the nucleic acid sequence encoding such protein, for example, as depicted in SEQ ID NO:2, will be preceded by a start codon. In case the 7-epizingiberene synthase protein of the present invention is preceded by a targeting sequence, said methionine will be encoded for within the targeting peptide.

7-epizingiberene synthase variants may comprise conservative amino acid substitutions within the categories basic (e.g. Arg, His, Lys), acidic (e.g. Asp, Glu), nonpolar (e.g. Ala, Val, Trp, Leu, Ile, Pro, Met, Phe, Trp) or polar (e.g. Gly, Ser, Thr, Tyr, Cys, Asn, Gln). In addition non-conservative amino acid substitutions fall within the scope of the invention.

The functionality of any 7-epizingiberene synthase protein, variant or fragment, can be determined using various methods. For example, transient or stable overexpression in plant cells can be used to test whether the protein has activity, i.e. provides enhanced insect pest resistance, in planta. Functionality is preferably tested in *Solanum lycopersicum*. Thus, for example transient or stable expression can be used to determine whether insect pest resistance is enhanced, indicating functionality.

"Fragments" of 7-epizingiberene synthase proteins and of variants of 7-epizingiberene synthase proteins, as described above, comprise fragments of 100, 150, 200, 300, 400, 500, 600, 700, contiguous amino acids or more, such as 777. Preferably, such fragments are functional in plant tissue, i.e. they are capable of conferring or enhancing insect pest resistance when produced in plant cells.

In another embodiment isolated nucleic acid sequences encoding any of the above proteins, variants or fragments are provided, such as cDNA, genomic DNA and RNA sequences. Due to the degeneracy of the genetic code various nucleic acid sequences may encode the same amino acid sequence. Any nucleic acid sequence encoding 7-epizingiberene synthase proteins or variants thereof are herein referred to as "7-epizingiberene synthase encoding sequences". The nucleic acid sequences provided include naturally occurring, artificial or synthetic nucleic acid sequences. One such nucleic acid sequence encoding a 7-epizingiberene synthase protein is provided in SEQ ID NO:2. It is understood that when sequences are depicted as DNA sequences while RNA is referred to, the actual base sequence of the RNA molecule is identical with the difference that thymine (T) is replace by uracil (U).

Also included are variants and fragments of 7-epizingiberene synthase encoding nucleic acid sequences, such as nucleic acid sequences hybridizing to 7-epizingiberene synthase encoding nucleic acid sequences under stringent hybridization conditions as defined. Variants of 7-epizingiberene synthase encoding nucleic acid sequences also include nucleic acid sequences which have a sequence identity to SEQ ID NO:2 (over the entire length) of at least 96.5%, 97%, 98%, 99%, 99.5%, 99.8% or more. It is clear that many methods can be used to identify, synthesise or isolate variants or fragments of 7-epizingiberene synthase encoding nucleic acid sequences, such as nucleic acid hybridization, PCR technology, in silico analysis and nucleic acid synthesis, and the like.

The nucleic acid sequence, particularly DNA sequence, encoding the 7-epizingiberene synthase proteins of this invention can be inserted in expression vectors to produce high amounts of 7-epizingiberene synthase proteins, as described below. For optimal expression in a host the 7-epizingiberene synthase encoding DNA sequences can be codon-optimized by adapting the codon usage to that most preferred in host (such as plant) genes. In the case of the host being a plant, codon usage may be adapted particularly to genes native to the plant genus or species of interest (Bennetzen & Hall, 1982, J. Biol. Chem. 257, 3026-3031; Itakura et al., 1977 Science 198, 1056-1063) using available codon usage tables (e.g. more adapted towards expression in cotton, soybean corn or rice). Codon usage tables for various plant species are published for example by Ikemura (1993, In "Plant Molecular Biology Labfax", Croy, ed., Bios Scientific Publishers Ltd.) and Nakamura et al. (2000, Nucl. Acids Res. 28, 292) and in the major DNA sequence databases (e.g. EMBL at Heidelberg, Germany). Accordingly, synthetic DNA sequences can be constructed so that the same or substantially the same proteins are produced. Several techniques for modifying the codon usage to that preferred by the host cells can be found in patent and scientific literature. The exact method of codon usage modification is not critical for this invention.

Small modifications to a DNA sequence such as described above can be routinely made, i.e., by PCR-mediated mutagenesis (Ho et al., 1989, Gene 77, 51-59, White et al., 1989, Trends in Genet. 5, 185-189).

"Fragments" of 7-epizingiberene synthase encoding nucleic acid sequences include fragments of at least 10, 12, 15, 16, 18, 20, 30, 40, 50, 100, 200, 500, 1000, 1500, 2000, 2500 or more consecutive nucleotides of SEQ ID NO:2, or of variants of SEQ ID NO:2. Short fragments can for example be used as PCR primers or hybridization probes.

In another embodiment of the invention PCR primers and/or probes and kits for detecting the 7-epizingiberene synthase encoding DNA or RNA sequences are provided. Degenerate or specific PCR primer pairs to amplify 7-epizingiberene synthase encoding DNA from samples can be synthesized based on SEQ ID NO:2 (or variants thereof) as known in the art (see Dieffenbach and Dveksler (1995) PCR Primer: A Laboratory Manual, Cold Spring Harbor Laboratory Press, and McPherson at al. (2000) PCR-Basics: From Background to Bench, First Edition, Springer Verlag, Germany). For example, any stretch of 9, 10, 11, 12, 13, 14, 15, 16, 18 or more contiguous nucleotides of SEQ ID NO:2 (or the complement strand) may be used as primer or probe. Likewise, DNA fragments of SEQ ID NO:2 (or variants thereof) can be used as hybridization probes. A detection kit for 7-epizingiberene synthase encoding sequences may comprise primers specific for 7-epizingiberene synthase encoding sequences and/or probes specific for 7-epizingiberene synthase encoding sequences, and an associated protocol to use the primers or probe to detect specific for zingiberene synthase encoding DNA sequences in a sample. Such a detection kit may, for example, be used to determine, whether a plant has been transformed with a specific 7-epizingiberene synthase encoding gene (or part thereof) of the invention. Because of the degeneracy of the genetic code, some amino acid codons can be replaced by others without changing the amino acid sequence of the protein.

In yet another embodiment a method for identifying and using orthologs or alleles of the gene encoding *Solanum habrochaites* 7-epizingiberene synthase (SEQ ID NO:2) is provided. The method comprises the steps of:
  a) obtaining or identifying a nucleic acid sequence comprising at least 96.5% nucleic acid identity to SEQ ID NO:2 (or a higher percentage sequence identity, as indicated above),
  b) using the nucleic acid sequence of a) to generate expression and/or silencing vectors,
  c) using one or more vectors of b) to transform a plant or plant cell(s), preferably of the plant species from which the nucleic acid was obtained, d) analysing the capability of the transformed plant/plant tissue to pest resistance in order to determine or verify the gene function in planta and/or to generate transgenic plants having enhanced insect pest resistance;

e) optionally, selecting those alleles or orthologs for further use which confer enhanced pest resistance to the transgenic plant.

Chimeric Genes, Expression Vectors, Host Cells, and Recombinant Organisms

In one embodiment of the invention nucleic acid sequences encoding 7-epizingiberene synthase proteins (including variants or fragments), as described above, are used to make chimeric genes, and vectors comprising these for transfer of the chimeric gene into a host cell and production of the 7-epizingiberene synthase protein(s) in host cells, such as cells, tissues, organs or organisms derived from transformed cell(s). In an advantageous embodiment, the production of 7-epizingiberene synthase is employed for the production of 7-epizingiberene. Vectors for the production of 7-epizingiberene synthase protein (or protein fragments or variants) in plant cells are herein referred to as "expression vectors".

Suitable host cells for expression of polypeptides such as 7-epizingiberene synthase include prokaryotes, yeast, or higher eukaryotic cells. Appropriate cloning and expression vectors for use with bacterial, fungal, yeast, and mammalian cellular hosts are described, for example, in Pouwels et al., Cloning vectors: A Laboratory Manual, Elsevier, N.Y., (1985). Cell-free translation systems could also be employed to produce the proteins of the present invention using RNAs derived from nucleic acid sequences disclosed herein. In an embodiment, said host cell (over)produces farnesyl-diphosphate (also referred to as "FPP"). In a suitable embodiment, said host cell produces or overproduces 2Z,6Z-farnesyl-diphosphate (also referred to as "Z,Z-farnesyl pyrophosphate" or "zFPP"). The skilled person is capable of overproducing the substrate of the 7-epizingiberene synthase of the present invention to produce 7-epizingiberene.

Suitable prokaryotic host cells include gram-negative and gram-positive organisms, for example, *Escherichia coli* or *Bacilli*. Another suitable prokaryotic host cell is *Agrobacterium*, in particular *Agrobacterium tumefaciens*.

Proteins of the present invention can also be expressed in yeast host cells, for example from the *Saccharomyces* genus (e.g., *Saccharomyces cerevisiae*). Other yeast genera, such as *Pichia* or *Kluyveromyces*, can also be employed.

Alternatively, proteins of the present invention may be expressed in higher eukaryotic host cells, including plant cells, fungal cells, insect cells, and mammalian, optionally non-human, cells.

One embodiment of the invention is a non-human organism modified to comprise a nucleic acid sequence of the present invention. The non-human organism and/or host cell may be modified by any methods known in the art for gene transfer including, for example, the use of delivery devices such as lipids and viral vectors, naked DNA, electroporation, chemical methods and particle-mediated gene transfer. In an advantageous embodiment, the non-human organism is a plant.

Any plant may be a suitable host, such as monocotyledonous plants or dicotyledonous plants, but most preferably the host plant belongs to the family Solanaceae. For example, the plant belongs to the genus *Solanum* (including *Lycopersicon*), *Nicotiana*, *Capsicum*, *Petunia* and other genera. The following host species may suitably be used: Tobacco (*Nicotiana* species, e.g. *N. benthamiana, N. plumbaginifolia, N. tabacum*, etc.), vegetable species, such as tomato (*L. esculentum*, syn. *Solanum lycopersicum*) such as e.g. cherry tomato, var. *cerasiforme* or currant tomato, var. *pimpinellifolium*) or tree tomato (*S. betaceum*, syn. *Cyphomandra betaceae*), potato (*Solanum tuberosum*), eggplant (*Solanum melongena*), pepino (*Solanum muricatum*), cocona (*Solanum sessiliflorum*) and naranjilla (*Solanum quitoense*), peppers (*Capsicum annuum, Capsicum frutescens, Capsicum baccatum*), ornamental species (e.g. *Petunia hybrida, Petunia axillaries, P. integrifolia*), coffee (*Coffea*).

Alternatively, the plant may belong to any other family, such as to the Cucurbitaceae or Gramineae. Suitable host plants include for example maize/corn (*Zea* species), wheat (*Triticum* species), barley (e.g. *Hordeum vulgare*), oat (e.g. *Avena sativa*), sorghum (*Sorghum bicolor*), rye (*Secale cereale*), soybean (*Glycine* spp, e.g. *G. max*), cotton (*Gossypium* species, e.g. *G. hirsutum, G. barbadense*), *Brassica* spp. (e.g. *B. napus, B. juncea, B. oleracea, B. rapa*, etc), sunflower (*Helianthus annus*), safflower, yam, cassava, alfalfa (*Medicago sativa*), rice (*Oryza* species, e.g. *O. sativa* indica cultivar-group or japonica cultivar-group), forage grasses, pearl millet (*Pennisetum* spp. e.g. *P. glaucum*), tree species (*Pinus*, poplar, fir, plantain, etc), tea, *coffea*, oil palm, coconut, vegetable species, such as pea, zucchini, beans (e.g. *Phaseolus* species), cucumber, artichoke, asparagus, broccoli, garlic, leek, lettuce, onion, radish, turnip, Brussels sprouts, carrot, cauliflower, chicory, celery, spinach, endive, fennel, beet, fleshy fruit bearing plants (grapes, peaches, plums, strawberry, mango, apple, plum, cherry, apricot, banana, blackberry, blueberry, citrus, kiwi, figs, lemon, lime, nectarines, raspberry, watermelon, orange, grapefruit, etc.), ornamental species (e.g. Rose, Petunia, Chrysanthemum, Lily, Gerbera species), herbs (mint, parsley, basil, thyme, etc.), woody trees (e.g. species of *Populus, Salix, Quercus, Eucalyptus*), fibre species e.g. flax (*Linum usitatissimum*) and hemp (*Cannabis sativa*), or model organisms, such as *Arabidopsis thaliana*.

Preferred hosts are "crop plants" or "cultivated plants", i.e. plant species which is cultivated and bred by humans. A crop plant may be cultivated for food or feed purposes (e.g. field crops), or for ornamental purposes (e.g. production of flowers for cutting, grasses for lawns, etc.). A crop plant as defined herein also includes plants from which non-food products are harvested, such as oil for fuel, plastic polymers, pharmaceutical products, cork, fibres (such as cotton) and the like.

The construction of chimeric genes and vectors for, preferably stable, introduction of 7-epizingiberene synthase protein-encoding nucleic acid sequences into the genome of host cells is generally known in the art. To generate a chimeric gene the nucleic acid sequence encoding a 7-epizingiberene synthase protein (or variant or fragment thereof) is operably linked to a promoter sequence, suitable for expression in the host cells, using standard molecular biology techniques. The promoter sequence may already be present in a vector so that the 7-epizingiberene synthase nucleic acid sequence is simply inserted into the vector downstream of the promoter sequence. The vector is then used to transform the host cells and the chimeric gene is inserted in the nuclear genome or into the plastid, mitochondrial or chloroplast genome and expressed there using a suitable promoter (e.g., Mc Bride et al., 1995 Bio/Technology 13, 362; U.S. Pat. No. 5,693,507). In one embodiment a chimeric gene comprises a suitable promoter for expression in plant cells or microbial cells (e.g. bacteria), operably linked to a nucleic acid sequence encoding a 7-epizingiberene synthase protein according to the invention, optionally followed by a 3' nontranslated nucleic acid sequence. The bacteria may subsequently be used for plant transformation (*Agrobacterium*-mediated plant transformation).

The 7-epizingiberene synthase nucleic acid sequence, preferably a 7-epizingiberene synthase chimeric gene, encoding an functional 7-epizingiberene synthase protein can be stably inserted in a conventional manner into the nuclear genome of a single plant cell, and the so-transformed plant cell can be used in a conventional manner to produce a transformed plant that has an altered phenotype due to the presence of the 7-epizingiberene synthase protein in certain cells at a certain time. In this regard, a T-DNA vector, comprising a nucleic acid sequence encoding a zingiberene synthase protein, in Agrobacterium tumefaciens can be used to transform the plant cell, and thereafter, a transformed plant can be regenerated from the transformed plant cell using the procedures described, for example, in EP 0 116 718, EP 0 270 822, PCT publication WO84/02913 and published European Patent application EP 0 242 246 and in Gould et al. (1991, Plant Physiol. 95, 426-434). The construction of a T-DNA vector for Agrobacterium mediated plant transformation is well known in the art. The T-DNA vector may be either a binary vector as described in EP 0 120 561 and EP 0 120 515 or a co-integrate vector which can integrate into the Agrobacterium Ti-plasmid by homologous recombination, as described in EP 0 116 718.

Preferred T-DNA vectors each contain a promoter operably linked to a 7-epizingiberene synthase encoding nucleic acid sequence (e.g. encoding SEQ ID NO: 2) between T-DNA border sequences, or at least located to the left of the right border sequence. Border sequences are described in Gielen et al. (1984, EMBO J 3, 835-845). Of course, other types of vectors can be used to transform the plant cell, using procedures such as direct gene transfer (as described, for example in EP 0 223 247), pollen mediated transformation (as described, for example in EP 0 270 356 and WO85/01856), protoplast transformation as, for example, described in U.S. Pat. No. 4,684,611, plant RNA virus-mediated transformation (as described, for example in EP 0 067 553 and U.S. Pat. No. 4,407,956), liposome-mediated transformation (as described, for example in U.S. Pat. No. 4,536,475), and other methods. For tomato or tobacco transformation see also An G. et al., 1986, Plant Physiol. 81: 301-305; Horsch R. B. et al., 1988, In: Plant Molecular Biology Manual A5, Dordrecht, Netherlands, Kluwer Academic Publishers. pp 1-9; Koornneef M. et al., 1986, In: Nevins D. J. and R. A. Jones, eds. Tomato Biotechnology, New York, N.Y., USA, Alan R. Liss, Inc. pp 169-178). For potato transformation see e.g. Sherman and Bevan (1988, Plant Cell Rep. 7: 13-16).

Likewise, selection and regeneration of transformed plants from transformed cells is well known in the art. Obviously, for different species and even for different varieties or cultivars of a single species, protocols are specifically adapted for regenerating transformants at high frequency.

Besides transformation of the nuclear genome, also transformation of the plastid genome, preferably chloroplast genome, is included in the invention. One advantage of plastid genome transformation is that the risk of spread of the transgene(s) can be reduced. Plastid genome transformation can be carried out as known in the art, see e.g. Sidorov V A et al. 1999, Plant J. 19: 209-216 or Lutz K A et al. 2004, Plant J. 37(6):906-13.

The resulting transformed plant can be used in a conventional plant breeding scheme to produce more transformed plants containing the transgene. Single copy transformants can be selected, using e.g. Southern Blot analysis or PCR based methods or the Invader® Technology assay (Third Wave Technologies, Inc.). Alternatively, the amount of 7-epizingiberene may be determined using analytical methods such as GC-MS. Transformed cells and plants can easily be distinguished from non-transformed ones by the presence of the chimeric gene. The sequences of the plant DNA flanking the insertion site of the transgene can also be sequenced, whereby an "Event specific" detection method can be developed, for routine use. See for example WO0141558, which describes elite event detection kits (such as PCR detection kits) based for example on the integrated sequence and the flanking (genomic) sequence.

The 7-epizingiberene synthase nucleic acid sequence may be inserted in a plant cell genome so that the inserted coding sequence is downstream (i.e. 3') of, and under the control of, a promoter which can direct the expression in the plant cell. This is preferably accomplished by inserting the chimeric gene in the plant cell genome, particularly in the nuclear or plastid (e.g. chloroplast) genome.

As the constitutive production of the 7-epizingiberene synthase protein may lead to the induction of cell death and/or may lower yield (see e.g. Rizhsky and Mittler, Plant Mol Biol, 2001 46: 313-23), it is in one embodiment preferred to use a promoter whose activity is inducible. Examples of inducible promoters are wound-inducible promoters, such as the MPI promoter described by Cordera et al. (1994, The Plant Journal 6, 141), which is induced by wounding (such as caused by insect or physical wounding), or the COMPTII promoter (WO0056897) or the PR1 promoter described in U.S. Pat. No. 6,031,151. Alternatively the promoter may be inducible by a chemical, such as dexamethasone as described by Aoyama and Chua (1997, Plant Journal 11: 605-612) and in U.S. Pat. No. 6,063,985 or by tetracycline (TOPFREE or TOP 10 promoter, see Gatz, 1997, Annu Rev Plant Physiol Plant Mol Biol. 48: 89-108 and Love et al. 2000, Plant J. 21: 579-88). Other inducible promoters are for example inducible by a change in temperature, such as the heat shock promoter described in U.S. Pat. No. 5,447,858, by anaerobic conditions (e.g. the maize ADH1S promoter), by light (U.S. Pat. No. 6,455,760), by pathogens (e.g. the gst1 promoter of EP759085 or the vst1 promoter of EP309862) or by senescence (SAG12 and SAG13, see U.S. Pat. No. 5,689,042). Obviously, there are a range of other promoters available.

In one embodiment, preferably, an insect pest inducible promoter is used, as thereby the 7-epizingiberene synthase protein (or variant or fragment) will only be produced following insect pest attack of the plant tissue. Especially, promoters of genes which are upregulated quickly after insect pest attack are desired. Promoters inducible by a particular plant insect pest may also be identified using known methods, such as cDNA-AFLP®.

Preferably, the promoter is inducible by a number of insect pests, i.e. it is inducible by a broad range of insect pests of the host plant. For each particular host plant species, a different promoter may be most suitable. For example, when tomato is used as a host, the promoter is preferably induced upon at least one, but preferably more than one tomato insect pest. Especially, a promoter which is inducible by one or more insect pests is preferred.

Detailed descriptions of plant insect pests, the disease symptoms caused by them and their life cycles can be found for each plant species. For example, tomato insect pests are described in "Compendium of Tomato Diseases", Editors Jones, Jones, Stall and Zitter, ISBN 0-89054-120-5, APS Press.

Alternatively, a host plant may comprise various 7-epizingiberene synthase transgenes, each under control of a different pest inducible promoter, to ensure that 7-epizingiberene synthase protein is produced following attack by a variety of insect pests. For example, for transformation of tomato, one promoter may be inducible by whitefly and one promoter may be inducible by aphids.

The word "inducible" does not necessarily require that the promoter is completely inactive in the absence of the inducer stimulus. A low level non-specific activity may be present, as long as this does not result in severe yield or quality penalty of the plants. Inducible, thus, preferably refers to an increase in activity of the promoter, resulting in an increase in transcription of the downstream zingiberene synthase coding region following contact with the inducer.

In another embodiment constitutive promoters may be used, such as the strong constitutive 35S promoters or enhanced 35S promoters (the "35S promoters") of the cauliflower mosaic virus (CaMV) of isolates CM 1841 (Gardner et al., 1981, Nucleic Acids Research 9, 2871-2887), CabbB-S (Franck et al., 1980, Cell 21, 285-294) and CabbB-JI (Hull and Howell, 1987, Virology 86, 482-493); the 35S promoter described by Odell et al. (1985, Nature 313, 810-812) or in U.S. Pat. No. 5,164,316, promoters from the ubiquitin family (e.g. the maize ubiquitin promoter of Christensen et al., 1992, Plant Mol. Biol. 18, 675-689, EP 0 342 926, see also Cornejo et al. 1993, Plant Mol. Biol. 23, 567-581), the gos2 promoter (de Pater et al., 1992 Plant J. 2, 834-844), the emu promoter (Last et al., 1990, Theor. Appl. Genet. 81, 581-588), *Arabidopsis* actin promoters such as the promoter described by An et al. (1996, Plant J. 10, 107), rice actin promoters such as the promoter described by Zhang et al., (1991, The Plant Cell 3, 1155-1165) and the promoter described in U.S. Pat. No. 5,641,876 or the rice actin 2 promoter as described in WO070067; promoters of the Cassava vein mosaic virus (WO 97/48819, Verdaguer et al. 1998, Plant Mol. Biol. 37, 1055-1067), the pPLEX series of promoters from Subterranean Clover Stunt Virus (WO 96/06932, particularly the S7 promoter), a alcohol dehydrogenase promoter, e.g., pAdh1S (GenBank accession numbers X04049, X00581), and the TR1' promoter and the TR2' promoter (the "TR1' promoter" and "TR2' promoter", respectively) which drive the expression of the 1' and 2' genes, respectively, of the T-DNA (Velten et al., 1984, EMBO J 3, 2723-2730), the Figwort Mosaic Virus promoter described in U.S. Pat. No. 6,051,753 and in EP426641, histone gene promoters, such as the Ph4a748 promoter from *Arabidopsis* (PMB 8: 179-191), or others.

Alternatively, a promoter can be utilized which is not constitutive but rather is specific for one or more tissues or organs of the plant (tissue preferred/tissue specific, including developmentally regulated promoters), for example leaf preferred, epidermis preferred, root preferred, flower tissue e.g. tapetum or anther preferred, seed preferred, pod preferred, etc.), or trichome-specific promoters such MTS1 and MSK1 as disclosed in WO2009082208, whereby the 7-epizingiberene synthase gene is expressed only in cells of the specific tissue(s) or organ(s) and/or only during a certain developmental stage. For example, the 7-epizingiberene synthase gene(s) can be selectively expressed in the leaves of a plant by placing the coding sequence under the control of a light-inducible promoter such as the promoter of the ribulose-1, 5-bisphosphate carboxylase small subunit gene of the plant itself or of another plant, such as pea, as disclosed in U.S. Pat. No. 5,254,799 or *Arabidopsis* as disclosed in U.S. Pat. No. 5,034, 322.

In one embodiment the promoter of the 7-epizingiberene synthase gene of *Solanum habrochaites* (wild tomato species) provided by the present invention is used. For example, the promoter of the 7-epizingiberene synthase gene of *S. habrochaites* may be isolated and operably linked to the coding region encoding zingiberene synthase protein of SEQ ID NO:1. The 7-epizingiberene synthase gene promoter (the upstream transcription regulatory region of SEQ ID NO:2) can be isolated from *S. habrochaites* plants using known methods, such as TAIL-PCR (Liu et al. 1995, Genomics 25(3):674-81; Liu et al. 2005, Methods Mol Biol. 286:341-8), Linker-PCR, or Inverse PCR (IPCR).

The 7-epizingiberene synthase coding sequence is preferably inserted into the plant genome so that the coding sequence is upstream (i.e. 5') of suitable 3' end nontranslated region ("3'end" or 3'UTR). Suitable 3' ends include those of the CaMV 35S gene ("3' 35S"), the nopaline synthase gene ("3' nos") (Depicker et al., 1982 J. Molec. Appl. Genetics 1, 561-573), the octopine synthase gene ("3' ocs") (Gielen et al., 1984, EMBO J 3, 835-845) and the T-DNA gene 7 ("3' gene 7") (Velten and Schell, 1985, Nucleic Acids Research 13, 6981-6998), which act as 3'-untranslated DNA sequences in transformed plant cells, and others. In one embodiment the 3'UTR of the tomato 7-epizingiberene synthase gene of *Solanum habrochaites* (wild tomato species) is used. Introduction of the T-DNA vector into *Agrobacterium* can be carried out using known methods, such as electroporation or triparental mating.

A 7-epizingiberene synthase encoding nucleic acid sequence can optionally be inserted in the plant genome as a hybrid gene sequence whereby the 7-epizingiberene synthase sequence is linked in-frame to a (U.S. Pat. No. 5,254,799; Vaeck et al., 1987, Nature 328, 33-37) gene encoding a selectable or scorable marker, such as for example the neo (or nptII) gene (EP 0 242 236) encoding kanamycin resistance, so that the plant expresses a fusion protein which is easily detectable. Alternatively, a 7-epizingiberene encoding nucleic acid sequence can be introduced by means of co-tranformation with a gene encoding a selectable or scorable marker, or the two genes can be present on a single T-DNA All or part of a 7-epizingiberene synthase nucleic acid sequence, encoding a 7-epizingiberene synthase protein (or variant or fragment), can also be used to transform microorganisms, such as bacteria (e.g. *Escherichia coli, Pseudomonas, Agrobacterium, Bacillus*, etc.), fungi, or algae or insects, or to make recombinant viruses. Transformation of bacteria, with all or part of the 7-epizingiberene synthase encoding nucleic acid sequence of this invention, incorporated in a suitable cloning vehicle, can be carried out in a conventional manner, preferably using conventional electroporation techniques as described in Maillon et al. (1989, FEMS Microbiol. Letters 60, 205-210) and WO 90/06999. For expression in prokaryotic host cell, the codon usage of the nucleic acid sequence may be optimized accordingly (as described for plants above). Intron sequences should be removed and other adaptations for optimal expression may be made as known.

The DNA sequence of the 7-epizingiberene synthase encoding nucleic acid sequence can be further changed in a translationally neutral manner, to modify possibly inhibiting DNA sequences present in the gene part and/or by introducing changes to the codon usage, e.g., adapting the codon usage to that most preferred by plants, preferably the specific relevant plant genus, as described above.

In accordance with one embodiment of this invention, the 7-epizingiberene synthase proteins are targeted to intracellular organelles such as plastids, preferably chloroplasts, mitochondria, or are secreted from the cell, potentially optimizing protein stability and/or expression. Similarly, the protein may be targeted to vacuoles. Targeting to plastids is particularly attractive as overproduction of sesquiterpenes in the cytosol is usually toxic to cells, whereas overproduction of sesquiterpenes in plastids does not suffer from this problem. For this purpose, in one embodiment of this invention, the chimeric genes of the invention comprise a coding region encoding a signal or target peptide, linked to the 7-epizingiberene synthase protein coding region of the invention. The signal or target peptide may, for example, be the natural plastid targeting peptide of said 7-epizingiberene synthase, e.g., the amino acid sequence as depicted in SEQ ID NO:3 (coded for by the nucleic acid sequence of SEQ ID NO:4). Other preferred peptides to be included in the proteins of this invention are the transit peptides for chloroplast or other plastid targeting, especially duplicated transit peptide regions from plant genes whose gene product is targeted to the plastids, the optimized transit peptide of Capellades et al. (U.S. Pat. No. 5,635,618), the transit peptide of ferredoxin-NADP+oxidoreductase from spinach (Oelmuller et al., 1993, Mol. Gen. Genet. 237, 261-272), the transit peptide described in Wong et al. (1992, Plant Molec. Biol. 20, 81-93) and the targeting peptides in published PCT patent application WO 00/26371. Also preferred are peptides signalling secretion of a protein linked to such peptide outside the cell, such as the secretion signal of the potato proteinase inhibitor II (Keil et al., 1986, Nucl. Acids Res. 14, 5641-5650), the secretion signal of the alpha-amylase 3 gene of rice (Sutliff et al., 1991, Plant Molec. Biol. 16, 579-591) and the secretion signal of tobacco PR1 protein (Cornelissen et al., 1986, EMBO J. 5, 37-40). Particularly useful signal peptides in accordance with the invention include the chloroplast transit peptide (e.g. Van Den Broeck et al., 1985, Nature 313, 358), or the optimized chloroplast transit peptide of U.S. Pat. No. 5,510,471 and U.S. Pat. No. 5,635,618 causing transport of the protein to the chloroplasts, a secretory signal peptide or a peptide targeting the protein to other plastids, mitochondria, the ER, or another organelle. Signal sequences for targeting to intracellular organelles or for secretion outside the plant cell or to the cell wall are found in naturally targeted or secreted proteins, preferably those described by Klösgen et al. (1989, Mol. Gen. Genet. 217, 155-161), Klösgen and Weil (1991, Mol. Gen. Genet. 225, 297-304), Neuhaus & Rogers (1998, Plant Mol. Biol. 38, 127-144), Bih et al. (1999, J. Biol. Chem. 274, 22884-22894), Morris et al. (1999, Biochem. Biophys. Res. Commun. 255, 328-333), Hesse et al. (1989, EMBO J. 8, 2453-2461), Tavladoraki et al. (1998, FEBS Lett. 426, 62-66), Terashima et al. (1999, Appl. Microbiol. Biotechnol. 52, 516-523), Park et al. (1997, J. Biol. Chem. 272, 6876-6881), Shcherban et al. (1995, Proc. Natl. Acad. Sci USA 92, 9245-9249).

To allow secretion of the 7-epizingiberene synthase proteins to the outside of the transformed host cell, an appropriate secretion signal peptide may be fused to the amino terminal end (N-terminal end) of the 7-epizingiberene synthase protein. Putative signal peptides can be detected using computer based analysis, using programs such as the program Signal Peptide search (SignalP V3.0) (Von Heijne, Gunnar, 1986 and Nielsen et al., 1996).

In one embodiment, several 7-epizingiberene synthase encoding nucleic acid sequences are co-expressed in a single host, preferably under control of different promoters. Alternatively, several 7-epizingiberene synthase protein encoding nucleic acid sequences can be present on a single transformation vector or be co-transformed at the same time using separate vectors and selecting transformants comprising both chimeric genes. Similarly, one or more 7-epizingiberene synthase encoding genes may be expressed in a single plant together with other chimeric genes, for example encoding other proteins which enhance insect pest resistance, or others.

It is understood that the different proteins can be expressed in the same plant, or each can be expressed in a single plant and then combined in the same plant by crossing the single plants with one another. For example, in hybrid seed production, each parent plant can express a single protein. Upon crossing the parent plants to produce hybrids, both proteins are combined in the hybrid plant.

Preferably, for selection purposes but also for weed control options, the transgenic plants of the invention are also transformed with a DNA encoding a protein conferring resistance to herbicide, such as a broad-spectrum herbicide, for example herbicides based on glufosinate ammonium as active ingredient (e.g. Liberty® or BASTA; resistance is conferred by the PAT or bar gene; see EP 0 242 236 and EP 0 242 246) or glyphosate (e.g. RoundUp®; resistance is conferred by EPSPS genes, see e.g. EPO 508 909 and EP 0 507 698). Using herbicide resistance genes (or other genes conferring a desired phenotype) as selectable marker further has the advantage that the introduction of antibiotic resistance genes can be avoided.

Alternatively, other selectable marker genes may be used, such as antibiotic resistance genes. As it is generally not accepted to retain antibiotic resistance genes in the transformed host plants, these genes can be removed again following selection of the transformants. Different technologies exist for removal of transgenes. One method to achieve removal is by flanking the chimeric gene with lox sites and, following selection, crossing the transformed plant with a CRE recombinase-expressing plant (see e.g. EP506763B1). Site specific recombination results in excision of the marker gene. Another site specific recombination systems is the FLP/FRT system described in EP686191 and U.S. Pat. No. 5,527, 695. Site specific recombination systems such as CRE/LOX and FLP/FRT may also be used for gene stacking purposes. Further, one-component excision systems have been described, see e.g. WO9737012 or WO9500555).

The present invention encompasses a method for preparing a 7-epizingiberene synthase comprising the step of culturing a host cell comprising at least one nucleic acid molecule according to the present invention under conditions allowing the production of said 7-epizingiberene synthase.

Also, the present invention provides a method for preparing 7-epizingiberene and/or R-curcumene comprising the steps of: a) transforming a host cell with a nucleic acid molecule, chimeric gene or vector of the present invention; b) culturing said host cell under conditions permitting production of 7-epizingiberene; c) optionally, isolating the 7-epizingiberene produced in step b); and d) optionally, dehydrogenating the 7-epizingiberene produced to produce R-curcumene. The skilled person will be capable of routinely selecting conditions permitting production of 7-epizingiberene. The host cell may have been metabolically engineered to produce or overproduce Z,Z-farnesyl-diphosphate (zFPP), the substrate for the 7-epizingiberene synthase of the present invention, to produce 7-epizingiberene. The skilled person is capable of accomplishing overproduction of the substrate of the 7-epizingiberene synthase of the present invention to produce 7-epizingiberene. Similarly, a person skilled in the art will be capable of isolating the 7-epizingiberene produced using routine methods for isolation of volatiles.

When exposed to air, isolated 7-epizingiberene can spontaneously convert to R-curcumene. This was previously observed by Bleeker et al. (Phytochemistry. 2011 January; 72(1):68-73). Moreover, the same authors show that converting, for instance by controlled dehydrogenation of 7-epizingiberene resulted in pure R-curcumene. The skilled person is capable of selecting conditions permitting conversion of 7-epizingiberene into R-curcumene.

zFPP, the substrate for the 7-epizingiberene synthase of the present invention, may be produced or overproduced by any means known in the art. For example, it may be produced naturally in the host cell of choice. Alternatively, a nucleic acid sequence encoding a Z,Z-farnesyl diphosphate synthase (hereinafter also referred to as "zFPS") may be introduced into a host cell to achieve expression of zFPP in said host cell. Preferably, such host cell comprises a source of isopentenyl diphosphate ("IPP") and dimethylallyl diphosphate ("DMAPP").

An isolated or recombinant protein having Z,Z-FPS ("zFPS") activity derived from *Solanum habrochaites* is described in WO 2008/142318 (herein incorporated by reference) and can further be found in the GenBank accession no. ACJ38408.1. As used in the context of the present invention, the term "Z,Z-farnesyl diphosphate synthase" or "zFPS" denotes a protein having an amino acid sequence as depicted in SEQ ID NO:6 or a variant thereof having at least 80%, 85%, 90%, 91%, 92%, 93%, 94%, 95%, 96%, 97%, 98%, or 99% sequence identity to the amino acid sequence of SEQ ID NO:6, preferably over the full length.

The present invention therefore also relates to a method for producing 7-epizingiberene from zFPP in a host cell, comprising:
 a) introducing into said host cell a first nucleic acid sequence encoding a zFPS as described herein and a second nucleic acid sequence encoding the 7-epizingiberene synthase of the present invention;
 b) culturing the transformed cell in suitable conditions for the expression of said first and said second nucleic acid sequences; and,
 c) optionally, collecting the zFPP and/or the 7-epizingiberene contained in said cell and/or in the culture medium.

The first nucleic acid sequence and second nucleic acid sequence may be present in a single vector or may be present in separate vectors.

Transformed Plant Cells/Plants/Seeds and Uses of the Nucleic Acid Sequence and Proteins According to the Invention In the following part the use of the 7-epizingiberene synthase-encoding nucleic acid sequences according to the invention to generate transgenic plant cells, plants, plant seeds, etc. and any derivatives/progeny thereof, with an enhanced insect pest resistance phenotype is described.

A transgenic plant with enhanced insect pest resistance can be generated by transforming a plant host cell with a nucleic acid sequence encoding at least one 7-epizingiberene synthase protein under the control of a suitable promoter, as described above, and regenerating a transgenic plant from said cell.

Preferred promoters are promoters which are insect pest inducible, as described above.

Preferably, the transgenic plants of the invention comprise enhanced insect pest resistance against one or more insect pests, especially. Thus, for example transgenic tomato or potato plants comprise enhanced resistance to at least one, or more, of the insect species listed above.

"Insect pest resistance" or "increased/enhanced insect pest resistance" is used herein to refer to an enhanced ability of plants harbouring the nucleotide sequence of the present invention (compared to wild type or control plants not harbouring the nucleotide sequence of the present invention) to withstand the attack of one or more plant insect pests, or in other words, it refers to a significant reduction in disease symptoms in plants harbouring the nucleotide sequence of the present invention compared to plants not harbouring the nucleotide sequence of the present invention (or empty-vector transformed) controls. Insect pest resistance or enhanced insect pest resistance may be determined using a variety of methods. Often disease symptoms are scored visually (either in bioassays or in the field) by assessing the disease symptoms at one or more time points after infestation or contact with an insect pest. Alternative methods include methods whereby the insect pest is detected and optionally quantified. A (transgenic) plant may thus show enhanced insect pest resistance if the amount or number of insect pests detected in/on the tissue is significantly less compared to controls, or if the insect pest spread is significantly slower than in controls. Ultimately, a significant increase in average yield of plants harbouring the nucleotide sequence of the present invention (e.g. at least 1%, 2%, 5%, 10% or more) compared to controls, when grown under equivalent insect pest pressure (preferably in the field) provides an indirect measurement of enhanced insect pest resistance.

Thus, a plurality of plants harbouring the nucleotide sequence of the present invention, for example, transgenic plants, expressing the 7-epizingiberene synthase protein of the invention show enhanced insect pest resistance if they show a significant reduction of disease symptoms, compared to the plants not harbouring the nucleotide sequence of the present invention. Obviously, statistical analysis is required to determine whether significant difference exists. Preferably, one or more disease symptoms are on average at least 2%, 5%, 10%, 15%, 20%, 30%, 40%, 50%, or even 100% lower in 7-epizingiberene synthase encoding nucleic acid sequence-harbouring plants than in the control plants. As the disease assay is different for every host-insect pest combination, no specific protocol can be provided, but the skilled person knows how to determine whether plants harbouring the nucleotide sequence of the present invention show significantly enhanced disease resistance to one or more insect pests. Bioassays as known in the art for each plant-pest combination can be used to compare resistance of transgenic plants to suitable controls.

Generally, the role of 7-epizingiberene produced by the protein encoded by the amino acid sequence of SEQ ID NO:1 in resistance (toxicity and/or repellance) to insect pests will be determined through the use of choice and no-choice experiments. In particular, a choice test will be performed. In a choice test different life stages (e.g. larvae or adults) will be allowed to choose between (transgenic) plants that produce 7-epizingiberene (through expression of a nucleic acid sequence encoding the amino acid sequence of SEQ ID NO:1) and non-transgenic (or empty vector) plants. This test will determine the repellent activity of 7-epizingiberene produced by the protein of SEQ ID NO:1.

A no-choice test will also be performed to determine the toxic effects of 7-epizingiberene produced through the expression of a nucleic acid sequence encoding the amino acid sequence of SEQ ID NO:1. In these experiments, insect pest species are forced to eat from (transgenic) plants that produce 7-epizingiberene (through expression of a nucleic acid sequence encoding the amino acid sequence of SEQ ID NO:1) and non-transgenic (or empty vector) plants. Subsequently, the insect performance (e.g. growth, development or fitness) will be determined as a measure of toxicity.

It is also an embodiment to generate transgenic plants which express several 7-epizingiberene synthase proteins, preferably under the control of different promoters, such as different pest inducible promoters.

The disease resistance phenotype can be fine-tuned by expressing a suitable amount of 7-epizingiberene synthase protein at a suitable time and location. Such fine-tuning may be done by determining the most appropriate promoter for a particular host-pest combination and also by selecting transgenic "events" which show the desired expression level. A too low level of 7-epizingiberene synthase protein or too slow induction of 7-epizingiberene synthase protein production following insect pest attack may be insufficient to enhance disease resistance levels. On the other hand, a too high protein level or expression at times and locations devoid of insect pest attack, may result in agronomically undesired phenotypes and yield penalties. However, the skilled person can easily generate plants having enhanced disease resistance, but which at the same time are agronomical acceptable.

Plants harbouring the nucleotide sequence of the present invention expressing desired levels of the 7-epizingiberene synthase protein are selected by e.g. analysing copy number (Southern blot analysis), mRNA transcript levels, by analysing the presence and level of 7-epizingiberene synthase protein in various tissues (e.g. SDS-PAGE; ELISA assays, etc), or by determining the amount of 7-epizingiberene, using analytical methods such as GC-MS. For regulatory reasons, preferably single copy transformants are selected and the sequences flanking the site of insertion of the chimeric gene is analysed, preferably sequenced to characterize the "event". High or moderate 7-epizingiberene synthase-encoding nucleic acid sequence expressing transgenic events are selected for further crossing/backcrossing/selfing until a high performing elite event with a stable 7-epizingiberene synthase-encoding nucleic acid sequence transgene is obtained.

Transformants expressing one or more 7-epizingiberene synthase genes according to the invention may also comprise other transgenes, such as other genes conferring disease resistance or conferring tolerance to other biotic and/or abiotic stresses. To obtain such plants with "stacked" transgenes, other transgenes may either be introgressed into the 7-epizingiberene synthase-encoding nucleic acid sequence transformants, or 7-epizingiberene synthase-encoding nucleic acid sequence transformants may be transformed subsequently with one or more other genes, or alternatively several chimeric genes may be used to transform a plant line or variety. For example, several chimeric genes may be present on a single vector, or may be present on different vectors which are co-transformed.

In one embodiment the following genes are combined with one or more 7-epizingiberene synthase genes according to the invention: known disease resistance genes, especially genes conferring enhanced resistance to pathogens, virus resistance genes, abiotic stress resistance genes (e.g. drought tolerance, salt tolerance, heat- or cold tolerance, etc.), herbicide resistance genes, and the like. The stacked transformants may thus have an even broader biotic and/or abiotic stress tolerance, to pathogen resistance, nematode resistance, salinity, cold stress, heat stress, water stress, etc. Also, 7-epizingiberene synthase-encoding nucleic acid sequence silencing approaches may be combined with 7-epizingiberene synthase-encoding nucleic acid sequence expression approaches in a single plant. For example, 7-epizingiberene synthase-encoding nucleic acid sequence overexpression in roots or tubers may confer or enhance root or tuber resistance to soil pests.

It is also possible to introduce or introgress the 7-epizingiberene synthase gene into a plant breeding line which already has a certain level of insect pest resistance. For durability of insect pest resistance in the field, it may be desirable to stack several disease resistance mechanisms in a plant, preferably whereby the resistance sources have different underlying molecular mechanisms.

Whole plants, seeds, cells, tissues and progeny (such as F1 hybrids, F2 seeds/plants, etc.) of any of the transformed plants described above are encompassed herein and can be identified by the presence of the transgene in the DNA, for example by PCR analysis using total genomic DNA as template and using zingiberene synthase-encoding nucleic acid sequence specific PCR primer pairs. Also "event specific" PCR diagnostic methods can be developed, where the PCR primers are based on the plant DNA flanking the inserted chimeric gene, see U.S. Pat. No. 6,563,026. Similarly, event specific AFLP fingerprints or RFLP fingerprints may be developed which identify the transgenic plant or any plant, seed, tissue or cells derived there from.

It is understood that the transgenic plants according to the invention preferably do not show non-desired phenotypes, such as yield reduction, enhanced susceptibility to diseases or undesired architectural changes (dwarfing, deformations) etc. and that, if such phenotypes are seen in the primary transformants, these can be removed by normal breeding and selection methods (crossing/backcrossing/selfing, etc.). Any of the transgenic plants described herein may be homozygous or hemizygous for the transgene.

The present invention also relates to a Solanum lycopersicum or Lycopersicon esculentum plant, plant cell, seed or fruit, comprising a nucleotide sequence encoding the amino acid sequence of SEQ ID NO:1 or an amino acid sequence comprising at least 92% amino acid sequence identity to the amino acid sequence of SEQ ID NO:1 over the entire length. Wild type Solanum lycopersicum does not produce detectable amounts of 7-epi-zingiberene. Using the nucleotide sequence of the present invention, it is possible to prepare a transgenic or non-transgenic Solanum lycopersicum plant, plant cell, seed or fruit having enhanced insect pest resistance. Preferably, said Solanum lycopersicum plant, plant cell, seed or fruit further comprises a nucleic acid sequence encoding a Z,Z-farnesyl diphosphate synthase.

Sequences Referred to

```
SEQ ID NO 1: amino acid sequence of the Solanum
habrochaites plastid zingiberene synthase protein.
CSHSTPSSMNGFEDARDRIRESFGKVELSPSSYDTAVVVAMVPSKHSLNE

PCFPQCLDWIIENQREDGSWGLNPSHPLLLKDSLSSTLACLLALTKWRVG

DEQIKRGLGFIETQSWAIDNKDQISPLGFEIIFPSMIKSAEKLNLNLAIN

KRDSTIKRALQNEFTRNIEYMSEGFGELCDWKEIIKLHQRQNGSLFDSPA

TTAAALIYHQHDKKCYEYLNSILQQHKNVVVPTMYPTKIHSLLCLVDTLQ

NLGVHRHFKSEIKKALDEIYRLWQQKNEEIFSNVTHCAMAFRLLRISYYD

VSSDELAEFVDEEHFFATSGKYTSHVEILELHKASQLAIDHEKDDILDKI

NNVVTRTFMEQKLLNNGFIDRMSKKEVELALRNFYIISDLAENRRYIKSY

EENNFKILKAAYRSPNINNKDLFIFSIRDFELCQAQHQEELQQLKRWFED

CRLDQLGLSEQFISASYLCAIPIVPGPELSDARLVYAKYVMLLTIVDDHF

ESFASTDECLNIIELVERWDDYASVGYKSERVKVLFSMFYKSIEEIATIA

EIKQGRSVKNHLINLWLKVMKLMLMERVEWCSGKTIPRIEEYLYVSSITF

GSRLIPLTTQYFIGIKISKDLLESDEIYGLCNFTGIVLRLLNDLQDSKRE

QKEGSINLVTLLMKSISEEEAIMKMKEILEMKRRELFKMVLVQKKGSQLP

QLCKEIFWRTCKWAHFTYSQTDRYRFPEEMENHIDEVFYKPLNH

SEQ ID NO 2: nucleic acid sequence of the Solanum
habrochaites zingiberene synthase gene (coding
sequence only).
TGCAGCCACAGTACCCCTTCATCAATGAATGGTTTCGAAGATGCAAGGGA

TAGAATAAGGGAAAGTTTTGGGAAAGTAGAGTTATCTCCTTCTTCCTATG
```

-continued

ACACAGCATGGGTAGCTATGGTCCCTTCAAAACATTCACTAAATGAGCCA

TGTTTTCCACAATGTTTGGATTGGATTATTGAAAATCAAAGAGAAGATGG

ATCTTGGGGACTAAACCCTAGCCATCCATTGCTTCTTAAGGACTCACTTT

CTTCCACTCTTGCATGTTTGCTTGCACTAACCAAATGGAGAGTTGGAGAT

GAGCAAATCAAAAGAGGCCTTGGCTTTATTGAAACCCAGAGTTGGGCAAT

TGATAACAAGGATCAAATTTCACCTCTAGGATTTGAAATTATATTTCCCA

GTATGATCAAGTCTGCAGAAAAACTAAACTTAAATCTAGCAATTAACAAA

AGAGATTCAACAATTAAAAGAGCATTACAGAATGAGTTCACGAGGAATAT

TGAATATATGAGTGAAGGATTTGGTGAATTATGTGATTGGAAGGAAATAA

TAAAGTTACATCAAAGGCAAATGGTTCATTATTTGATTCACCAGCCACT

ACTGCAGCTGCCTTGATTTACCATCAGCATGATAAAAAATGCTATGAATA

TCTTAATTCAATCTTGCAACAACACAAAAATTGGGTTCCCACTATGTATC

CAACAAAGATACATTCATTGCTTTGCTTGGTTGATACACTTCAAAATCTT

GGAGTACATCGGCATTTTAAATCAGAAATAAAGAAAGCCCTAGATGAAAT

ATACAGGCTATGGCAACAAAAGAATGAAGAAATTTTCTCAAATGTCACCC

ATTGTGCTATGGCTTTTCGACTTCTAAGGATAAGCTACTATGATGTCTCC

TCAGATGAACTAGCAGAATTTGTGGATGAAGAACATTTCTTTGCAACAAG

TGGGAAATATACAAGTCATGTTGAAATTCTTGAACTCCACAAAGCATCAC

AATTGGCTATTGATCATGAGAAAGATGACATTTTGGATAAGATTAACAAT

TGGACAAGAACATTTATGGAGCAAAAACTCTTAAACAATGGCTTCATAGA

TAGGATGTCAAAAAAGGAGGTGGAACTTGCTTTGAGGAATTTTTATATCA

TATCTGATCTAGCAGAAAATAGAAGATATATAAAGTCATACGAAGAGAAC

AATTTTAAAATCTTAAAAGCAGCTTATAGGTCACCTAACATTAACAATAA

GGACTTGTTTATATTTTCAATACGCGACTTTGAATTATGCCAAGCTCAAC

ACCAAGAAGAACTTCAACAACTCAAGAGGTGGTTTGAAGATTGTAGATTG

GACCAACTCGGACTTTCGGAACAATTTATATCTGCTAGTTACTTATGTGC

TATTCCTATTGTCCCCGGGCCTGAATTATCCGATGCTCGTCTCGTGTACG

CGAAATACGTCATGCTCTTGACTATTGTCGATGATCATTTCGAGAGTTTT

GCATCTACAGATGAATGTCTCAACATCATTGAATTAGTAGAAAGGTGGGA

TGACTATGCAAGTGTAGGTTATAAATCTGAGAGGGTTAAAGTTTTATTTT

CAATGTTTTACAAATCAATAGAGGAGATTGCAACAATTGCTGAAATTAAA

CAAGGACGATCTGTCAAAAATCACCTTATTAATTTGTGGCTTAAAGTGAT

GAAGTTGATGTTGATGGAACGAGTAGAGTGGTGTTCTGGCAAGACAATAC

CAAGAATAGAAGAGTATTTGTATGTTAGTTCTATAACATTTGGTTCAAGA

TTGATTCCTCTCACAACACAATATTTTATTGGAATAAAAATATCCAAAGA

TCTTTTAGAAAGTGATGAAATTTATGGTTTATGCAATTTTACCGGTATAG

TCTTGAGGCTCCTCAATGATTTACAAGATTCCAAGAGAGAACAAAAGGAG

GGCTCAATAAATTTAGTCACATTACTAATGAAAAGTATCTCTGAGGAAGA

AGCTATAATGAAGATGAAGGAAATCTTGGAAATGAAAAGAAGAGAGTTAT

TTAAAATGGTTTTAGTTCAAAAAAAGGGAAGCCAATTGCCTCAATTATGC

AAAGAAATATTTTGGAGGACATGCAAATGGGCTCATTTCACTTATTCACA

AACTGATAGATATAGATTTCCAGAGGAAATGGAGAATCACATTGATGAAG

TCTTTTACAAACCACTCAATCATTAA

SEQ ID NO: 3. Amino acid sequence of the plastid
targeting sequence of the zingiberene synthase of
the invention
MIVGYRSTIITLSHPKLGNGKTISSNAIFRRSCRVR SEQ ID NO: 4. Nucleic acid sequence of the plastid
targeting sequence of the zingiberene synthase of
the invention
ATGATAGTTGGCTATAGAAGCACAATCATAACCCTTTCTCATCCTAAGCT

AGGCAATGGGAAAACAATTTCATCCAATGCAATTTTCCGGAGATCATGTA

GAGTAAGA

SEQ ID NO: 5. Nucleic acid sequence of zFPS from
*S. habrochaites* PI127826
GCTCGTGGACTCAACAAGATTTCATGCTCACTCAGCTTACAAACCGAAAA

ACTTTGTTATGAGGATAATGATAATGATCTTGATGAAGAACTTATGCCTA

AACACATTGCTTTGATAATGGATGGTAATAGGAGATGGGCAAAGGATAAG

GGTTTAGACGTATCCGAAGGTCACAAACATCTCTTTCCAAAATTAAAAGA

GATTTGTGACATTTCTTCTAAATTGGGAATACAAGTTATCACTGCTTTTG

CATTCTCTACTGAAAATTGGAAACGAGCCAAGGGGGAGGTTGATTTCTTG

ATGCAAATGTTCGAAGAACTCTATGATGAGTTTTCGAGGTCTGGAGTAAG

AGTGTCTATTATTGGTTGTAAAACCGACCTCCCAATGACATTACAAAAAT

GCATAGCATTAACAGAAGAGACTACAAAGGGAAACAAAGGACTTCACCTT

GTGATTGCACTAAACTATGGTGGATATTATGACATATTGCAAGCAACAAA

AAGCATTGTTAATAAAGCAATGAATGGTTTATTAGATGTAGAAAATATCA

ACAAGAATTTATTTGATCAAGAACTTGAAAGCAAGTGTCCAAATCCTGAT

TTACTTATAAGGACAGGAGGTGTTCAAAGAGTTAGTAACTTTTTGTTGTG

GCAATTGGCTTATACTGAATTTTACTTCACCAAAACATTGTTTCCTGATT

TTGGAGAGGAAGATCTTAAAGAGGCAATAATAAACTTTCAACAAAGGCAT

AGACGTTTTGGTGGACACACATATTGA

SEQ ID NO: 6. Amino acid sequence of zFPS from *S.
habrochaites* PI127826
ARGLNKISCSLSLQTEKLCYEDNDNDLDEELMPKHIALIMDGNRRWAKDK

GLDVSEGHKHLFPKLKEICDISSKLGIQVITAFAFSTENWKRAKGEVDFL

MQMFEELYDEFSRSGVRVSIIGCKTDLPMTLQKCIALTEETTKGNKGLHL

VIALNYGGYYDILQATKSIVNKAMNGLLDVENINKNLFDQELESKCPNPD

LLIRTGGVQRVSNFLLWQLAYTEFYFTKTLFPDFGEEDLKEAIINFQQRH

RRFGGHTY

SEQ ID NO: 7. Signal peptide of zFPS from *S.
habrochaites* PI127826
MSSLVLQCWKLSSPSLILQQNTSISMGAFKGIHKLQIPNSPLTVS SEQ ID NO: 8 Nucleic acid sequence of the signal
peptide of zFPS from *S. habrochaites* PI127826
ATGAGTTCTTTGGTTCTTCAATGTTGGAAATTATCATCTCCATCTCTGATT

TTACAACAAAATACATCAATATCCATGGGTGCATTCAAAGGTATTCATAAA

CTTCAAATCCCAAATTCACCTCTGACAGTGTCT

FIGURES

FIG. 1 shows Gas Chromatography Mass Spectrometry (GCMS) results of production of 7-epizingiberene using zFPP as precursor by *E. coli* transformed with the nucleotide sequence encoding 7-epizingiberene synthase. 7-epizingiberene was identified by its MS ion mass fingerprint, retention time and Kovats index.

Enantioselective gas chromatography on the cyclodextrin coated column allowed identification of the different zingiberene stereoisomers (Astec CHIRALDEXTM B-DM column, Supelco). From top to bottom:
*S. habrochaites*=positive control for 7-epizingiberene;
F2 ShxSI=the F2 produces 7-epizingiberene with zFPP as precursor
gingeroil=positive control for alpha-zingiberene.
ShZIS+ginger oil=ShZIS with zFPP produces 7-epizingiberene and ginger oil contains alpha-zingiberene The figure indicates that ShZIS synthesizes 7-epizingiberene when provided with zFPP. Moreover, it shows evidence that F2 plants used in the bioassays also produce 7-epizingiberene.

Figure 3A:
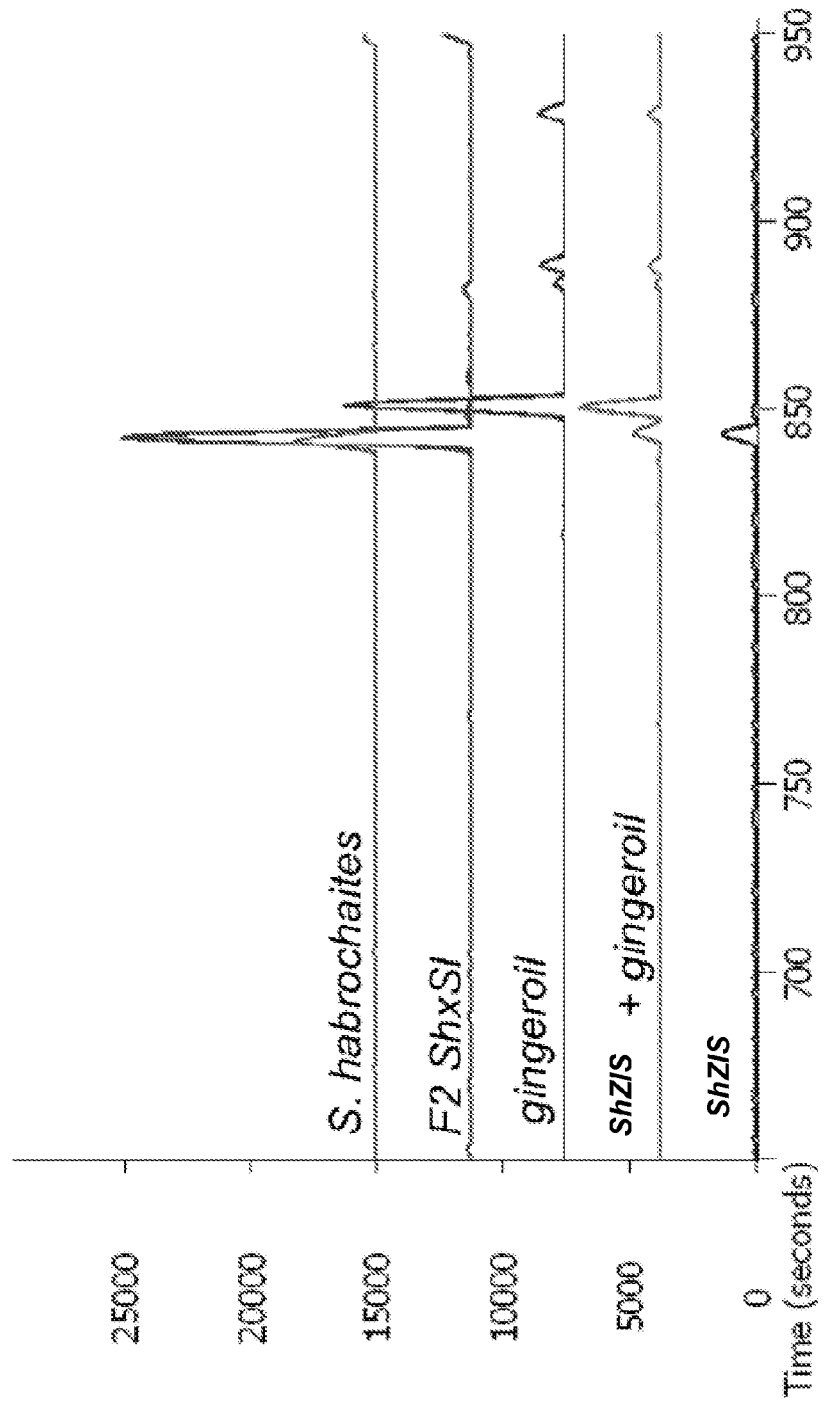
FIG. 3A shows the determination of the enantiomer of ShZIS
Figure 3B:
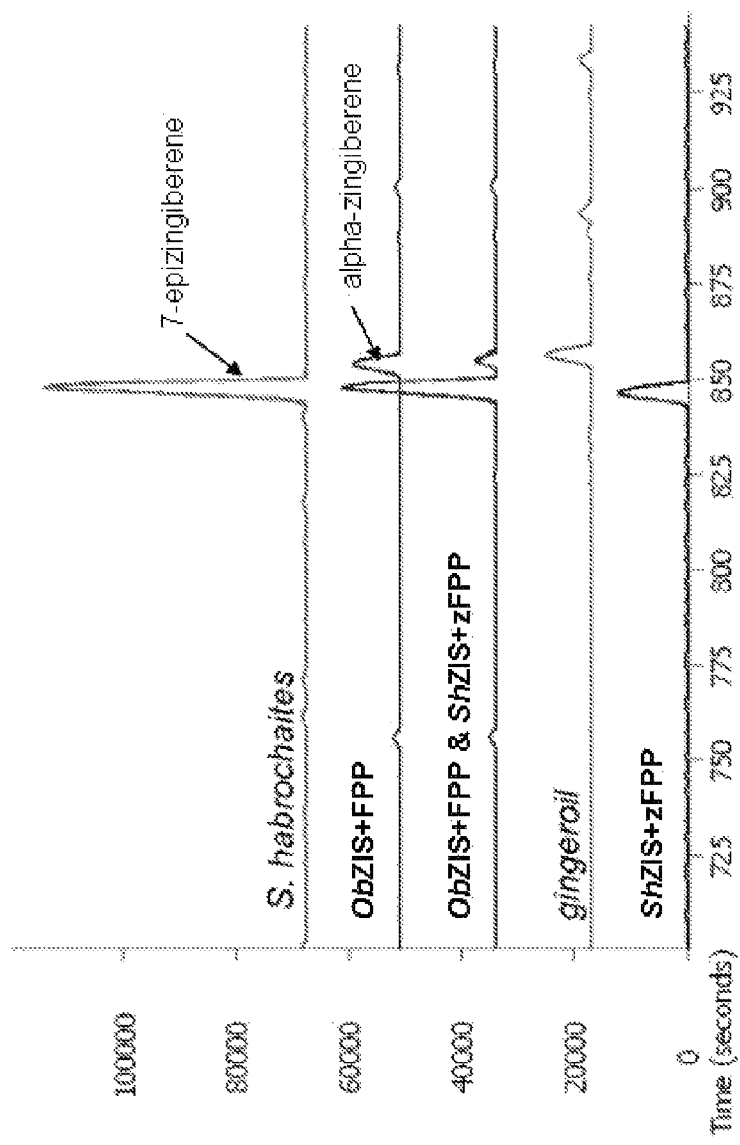

FIG. 3B shows the determination of the enantiomer of the zingiberene produced by ShZIS. Enantioselective gas chromatography on the cyclodextrin coated column allowed identification of the different zingiberene stereoisomers (Astec CHIRALDEXTM B-DM column, Supelco). From top to bottom:
*S. habrochaites*=positive control for 7-epizingiberene;
αZIS+FPP=alpha-zingiberene synthase provided with FPP yields α-zingiberene;
αZIS+FPP & ShZIS+zFPP=alpha-zingiberene synthase provided with FPP yields alpha-zingiberene and ShZIS synthesizes 7-epizingiberene when provided with zFPP.
Ginger oil=positive control for alpha-zingiberene.
ShZIS+zFPP=the protein ShZIS, when supplied with zFPP as a precursor produces 7-epizingiberene.

The figure indicates that ShZIS synthesizes 7-epizingiberene when provided with zFPP. Lemon basil zingiberene synthase (ObZIS; Iijima et al., 2004) is a bona-fide alpha-zingiberene synthase when provided with FPP.

FIG. 4 shows production of 7-epizingiberene in transgenic *S. lycopersicum* plants, when both zFPS and ShZIS are expressed under trichome specific promoters.

Figure 4A:
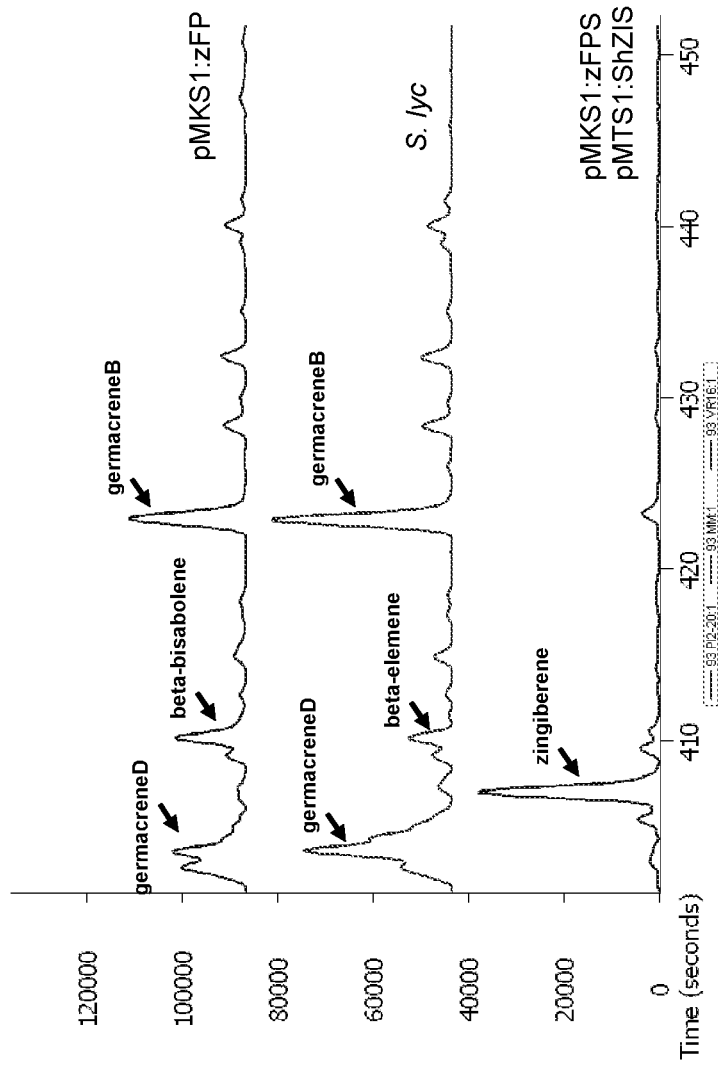

FIG. 4A. The production of 7-epizingiberene as measure by GCMS. Depicted are the terpenoid profiles of untransformed control (*S. lyc*) plants, *S. lycopersicum* plants transformed only with zFPS, and *S. lycopersicum* plants transformed with both zFPS and ShZIS under trichome-specific promoters. 7-epizingiberene was only produced in plants transformed with zFPS and ShZIS (both under trichome-specific promoters).

Figure 4B:
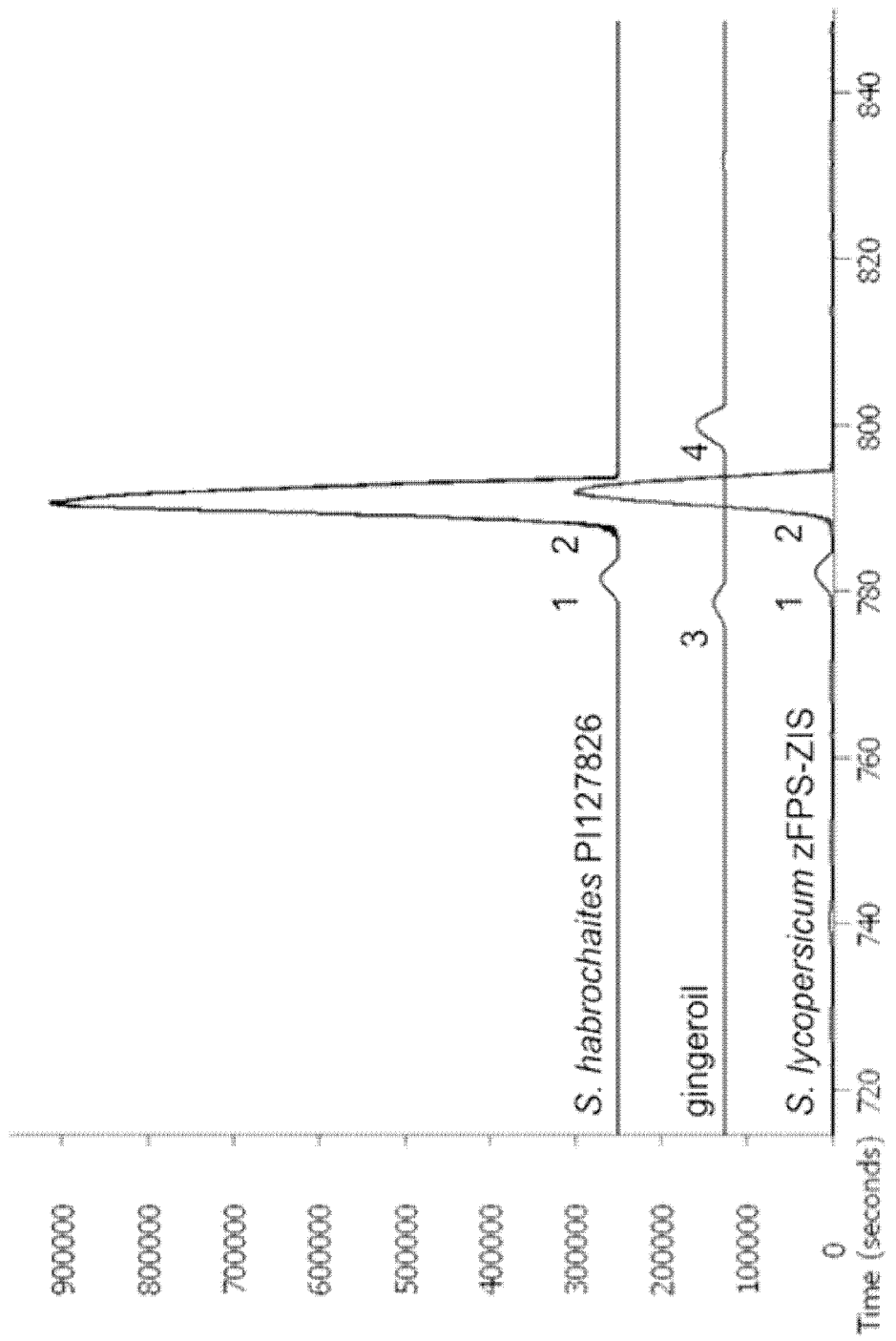

FIG. 4B. Enantioselective gas chromatography on the cyclodextrin coated column proved that zingiberene production in *S. lycopersicum* plants transformed with zFPS and ShZIS (*S. lycopersicum* zFPS-ZIS in the figure), like in wild *S. habrochaites*, is 7-epizingiberene.

Figure 5:
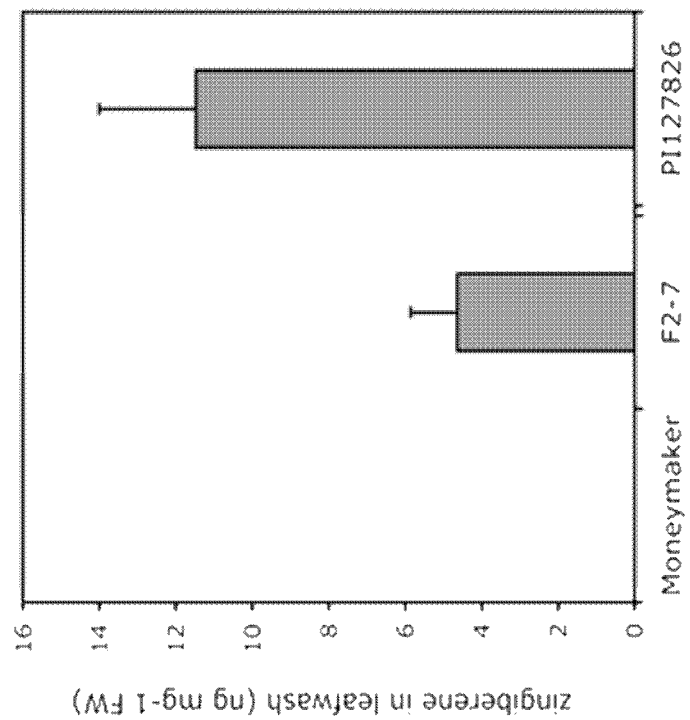

FIG. 5 shows the concentration of zingiberene (ng terpenes per mg leaf FW) in three different genotypes. An interspecies cross between *S. lycopersicum* and *S. habrochaites* was performed and F2 lines were tested for the production of zingiberene. Cuttings were made of zingiberene producing F2 lines, *S. lycopersicum* C32 (Moneymaker) and of *S. habrochaites* (PI127826). F2 and *S. habrochaites* (PI127826) plants showed similar amounts of 7-epizingiberene, no 7-epizingiberene was detectable in *S. lycopersicum* C32.

Figure 6A:
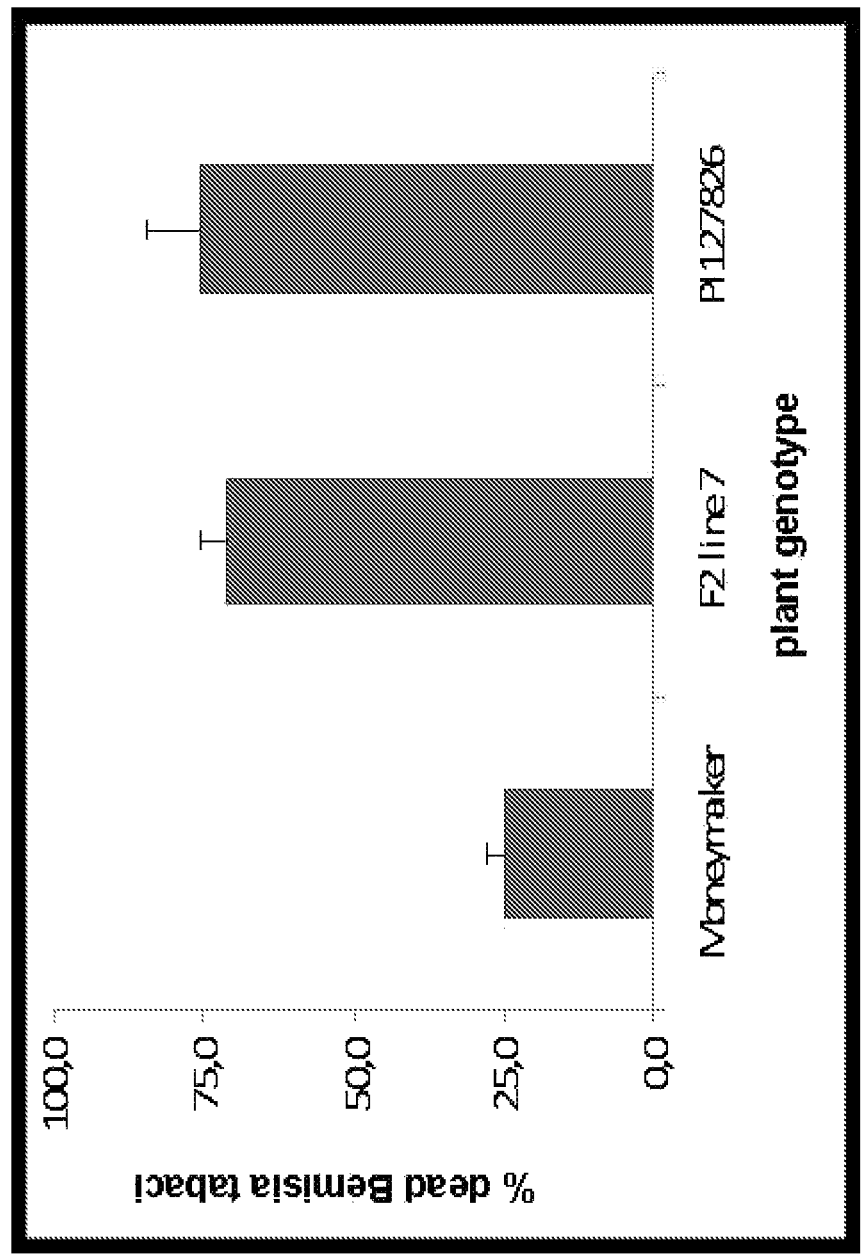

FIG. 6A shows the percentage of dead *B. tabaci* adults (mortality) in three different genotypes.

Clip cage experiments were performed on cuttings of F2 lines, *S. lycopersicum* C32 (Moneymaker) and of *S. habrochaites* (PI127826). Compared to *S. habrochaites* and F2 plants, the percentage dead adults after 5 days was significantly lower on *S. lycopersicum* (FIG. 4a; One-way ANOVA, LSD; $p<0.05$ for both comparisons).

Figure 6B:
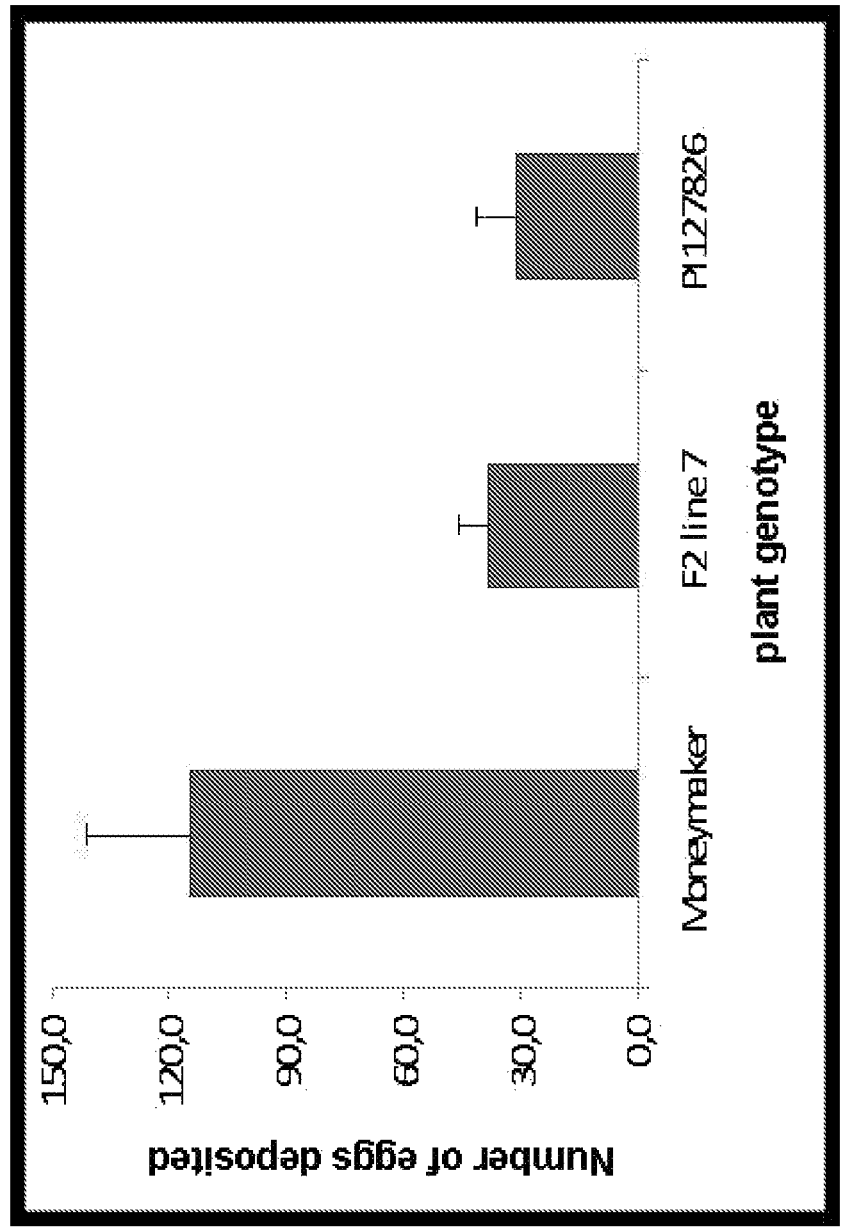

FIG. 6B shows the total number of eggs deposited by whitefly adults in five days.

Clip cage experiments were performed on cuttings of F2 lines, *S. lycopersicum* C32 and of *S. habrochaites* (PI127826). The number of eggs deposited by female *B. tabaci* adults was significantly higher on *S. lycopersicum* C32 compared to either F2 or *S. habrochaites* plants (FIG. 4b; One-way ANOVA, LSD; $p<0.05$ for both comparisons).

Figure 7A:
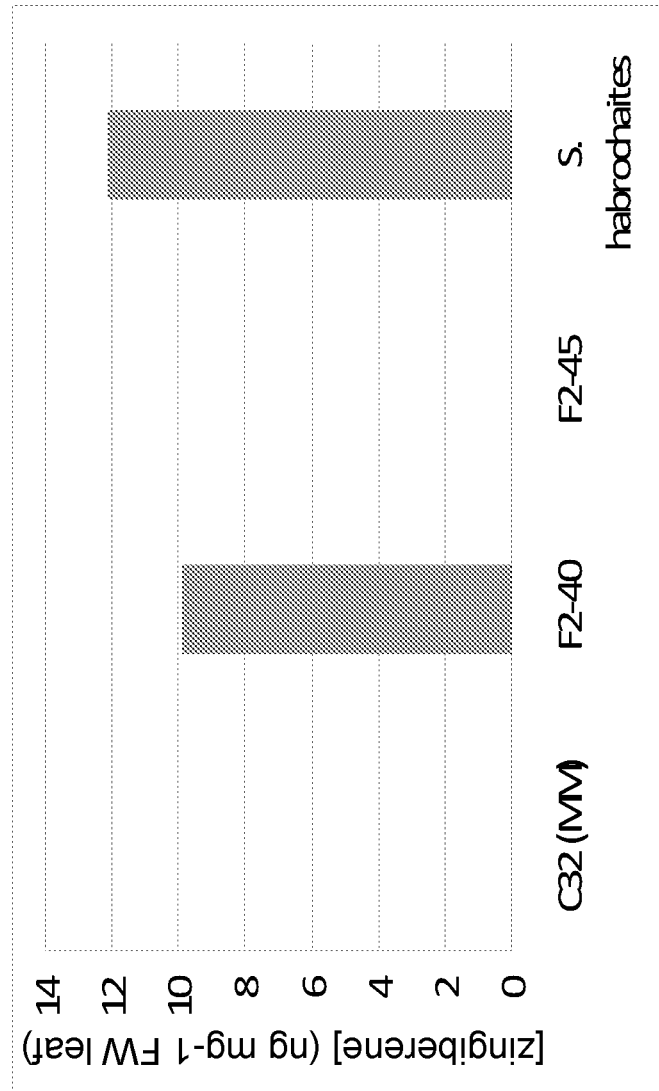

FIG. 7A shows 7-epizingiberene levels F2 plants expressed as [zingiberene] (ng mg-1 FW leaf).

Figure 7B:
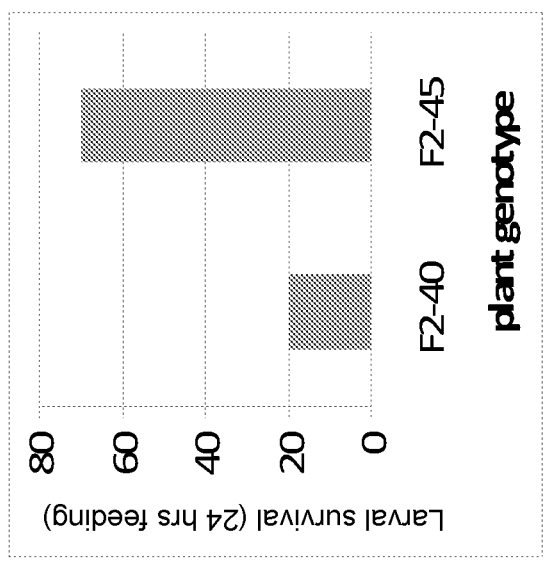

FIG. 7B shows Colorado Potato Beetle (CPB) neonate larvae survival in a bio-assay (24 hrs feeding).

Figure 7C:
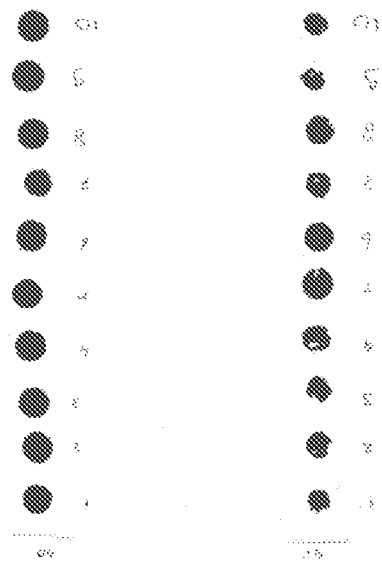

FIG. 7C shows feeding damage by CPB—24 hrs of feeding.

Figure 7D:
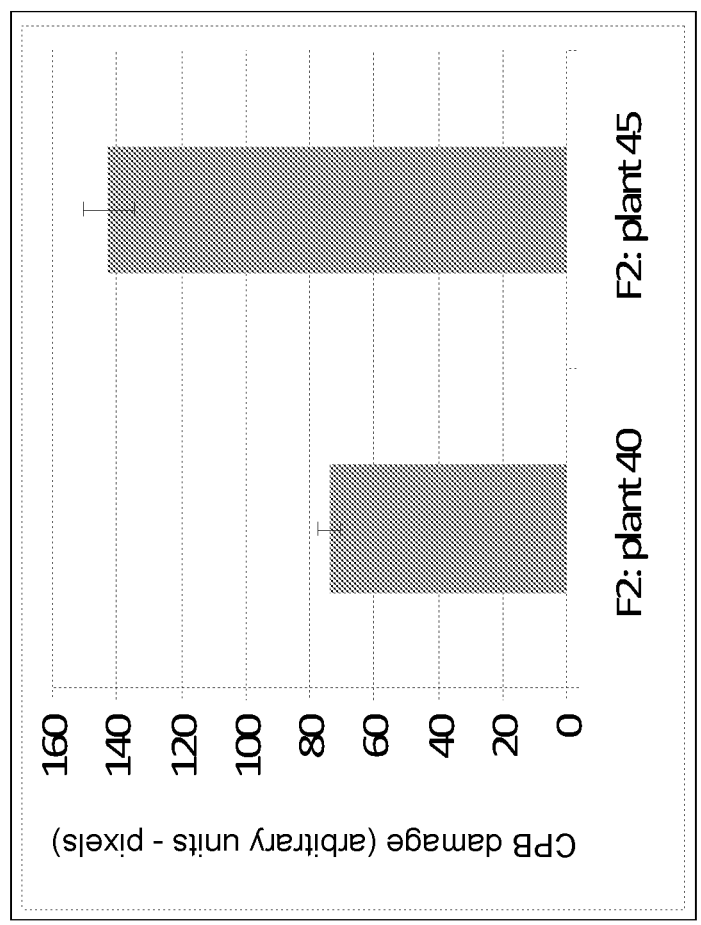

FIG. 7D shows feeding damage by CPB—24 hrs of feeding—damage is classified as arbitrary units (pixels).

Figure 8:
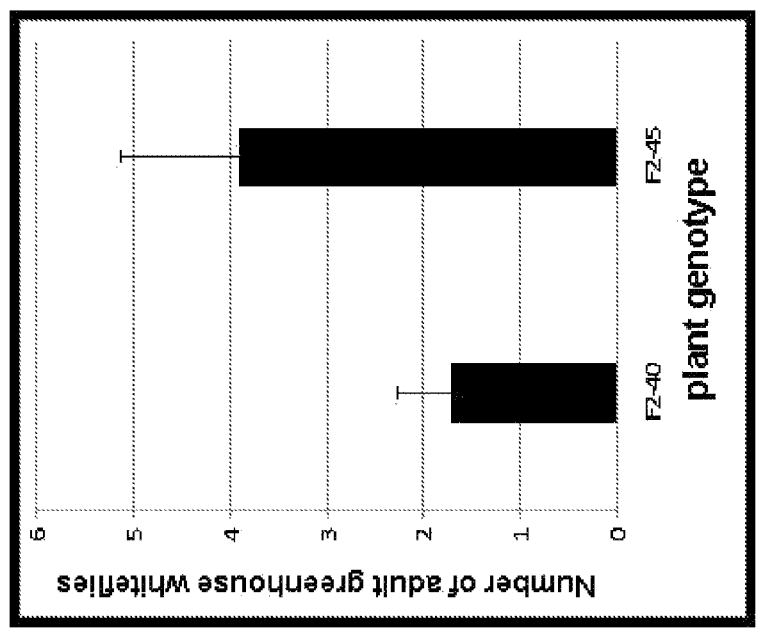

FIG. 8 demonstrates the preference of the Greenhouse whitefly (*Trialeurodes vaporariorum*) preference in a choice-assay for low 7-epizingiberene producing plants (line F2-45) over high 7-epizingiberene (line F2-40) plants.

Figure 9:
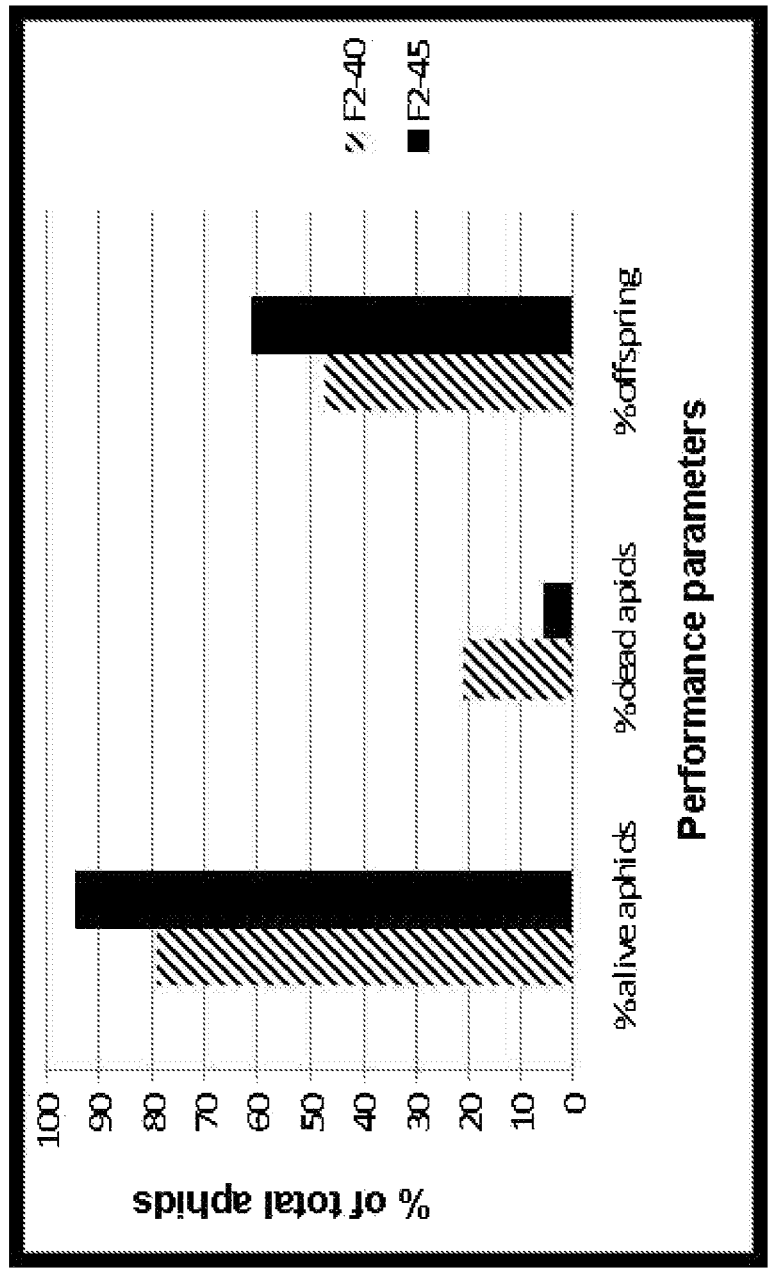

FIG. 9 shows performance of the potato/tomato aphid (*Macrosiphum euphorbiae*) in a no-choice-assay between low 7-epizingiberene producing plants (line F2-45) and high 7-epizingiberene producing (line F2-40) plants.

Figure 10A:
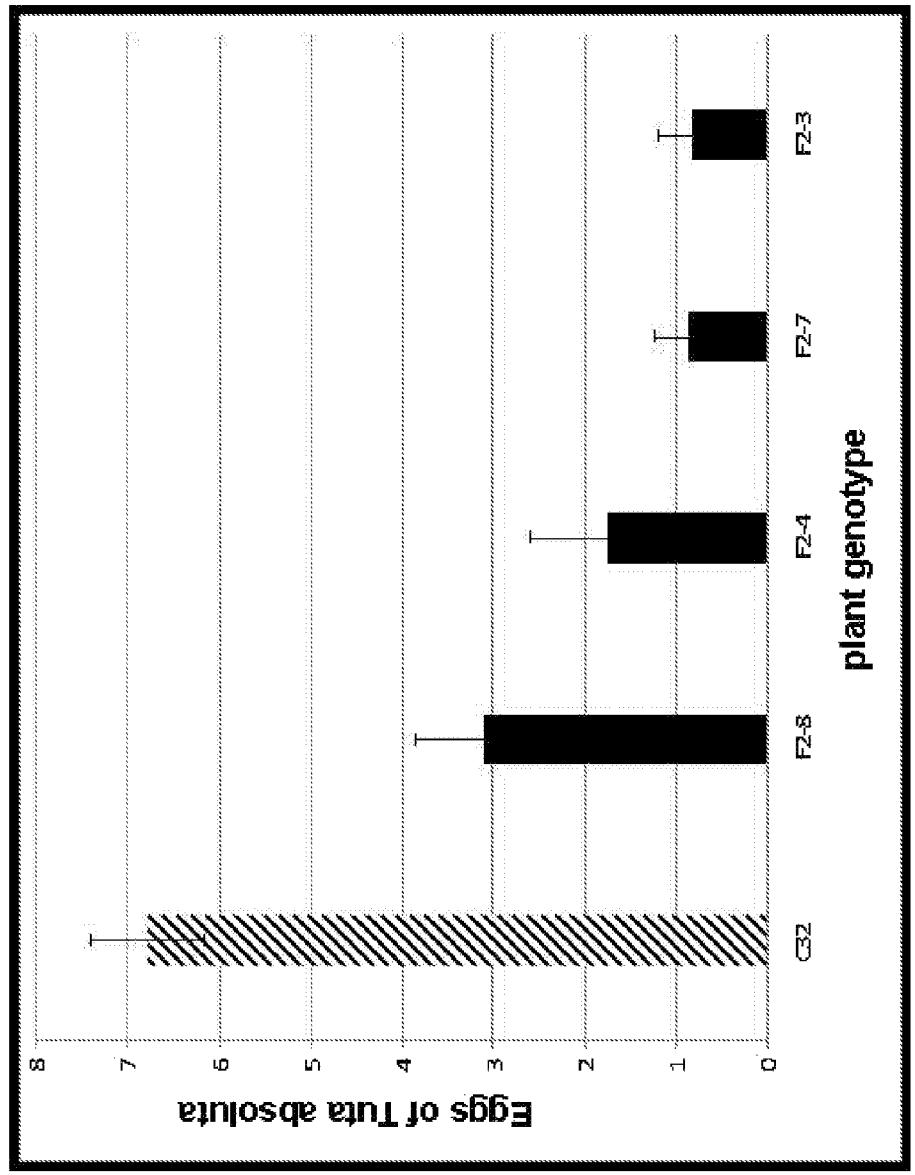

FIG. 10A demonstrates oviposition of *Tuta absoluta*. *Tuta absoluta* moths were released in a cage on F2 plants that produced a range of 7-epizingiberene. These plants have arisen from an interspecies cross between *S. lycopersicum* (C32) and *S. habrochaites* (PI127826). The number of eggs per tomato genotype was determined after 5 days.

Figure 10B:
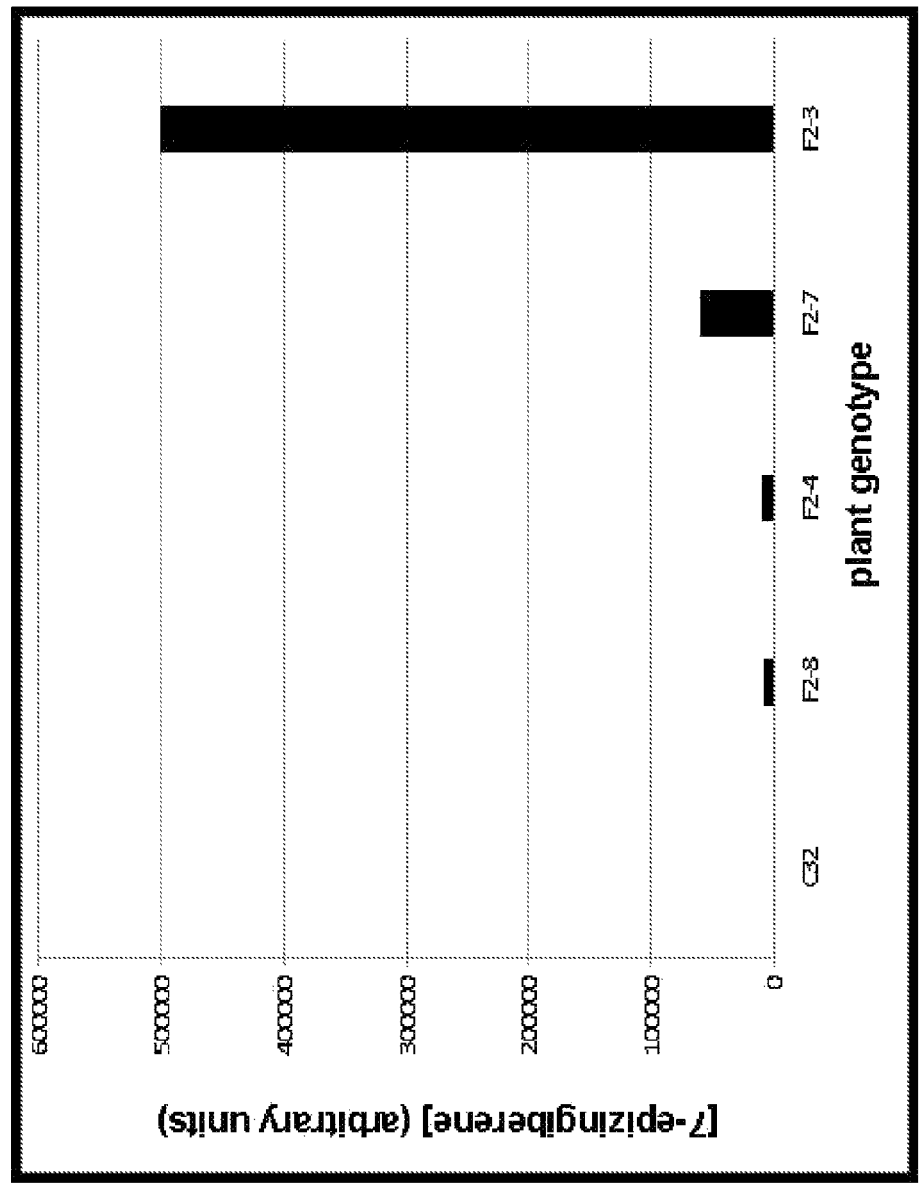

FIG. 10B shows production of 7-epizingiberene in these F2 plants arisen from an interspecies cross between *S. lycopersicum* (C32) and *S. habrochaites* (PI127826).

Figure 11A:
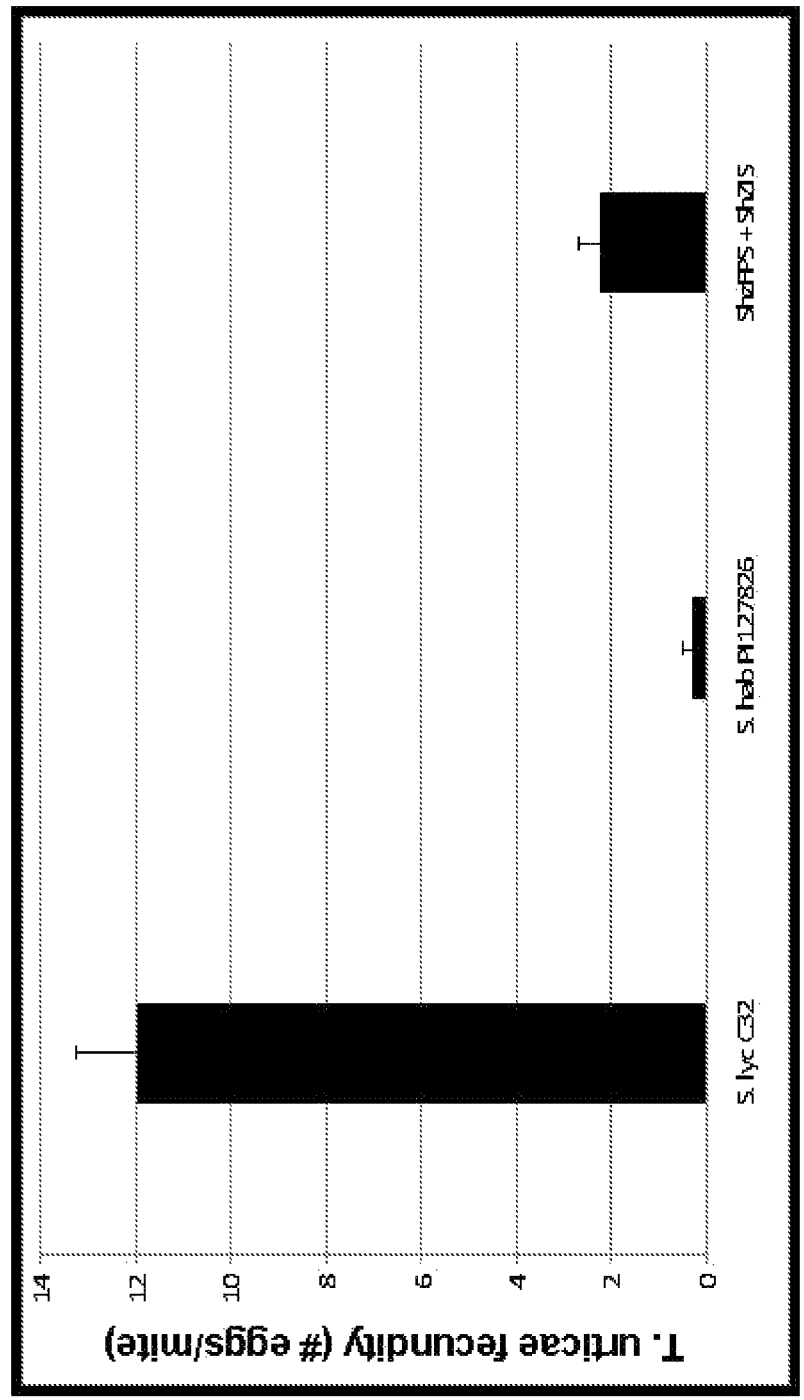

FIG. 11A demonstrates Spider mite (*T. urticae*) fecundity on *S. lycopersicum* (C32), 7-epi-zingiberene producing transgenic *S. lycopersicum* (line 2) and *S. habrochaites* (PI127826).

Figure 11B:
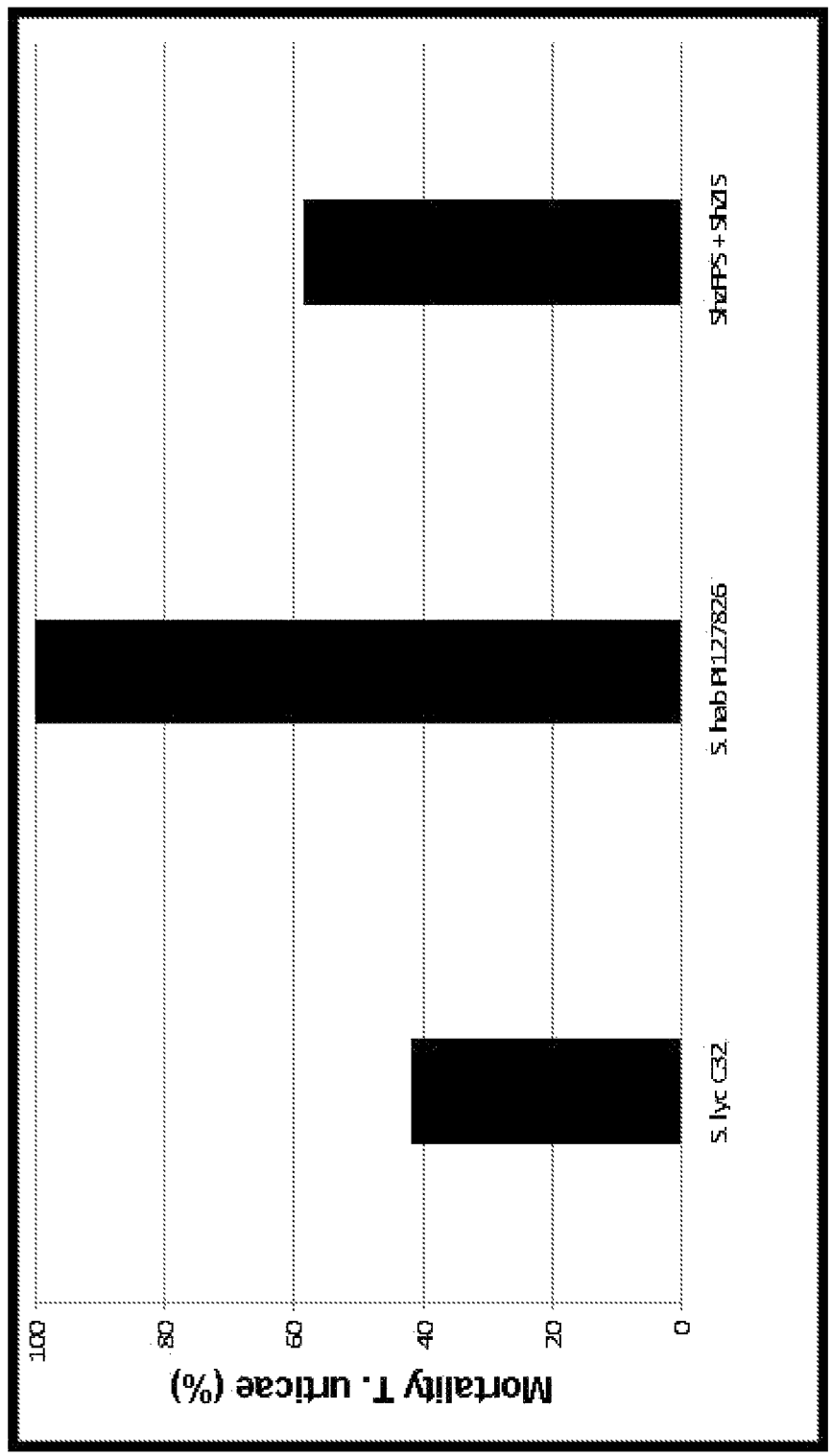

FIG. 11B shows Spider mite (*T. urticae*) survival on *S. lycopersicum* (C32), 7-epi-zingiberene producing transgenic *S. lycopersicum* (line 2) and *S. habrochaites* (PI127826).

Figure 11C:
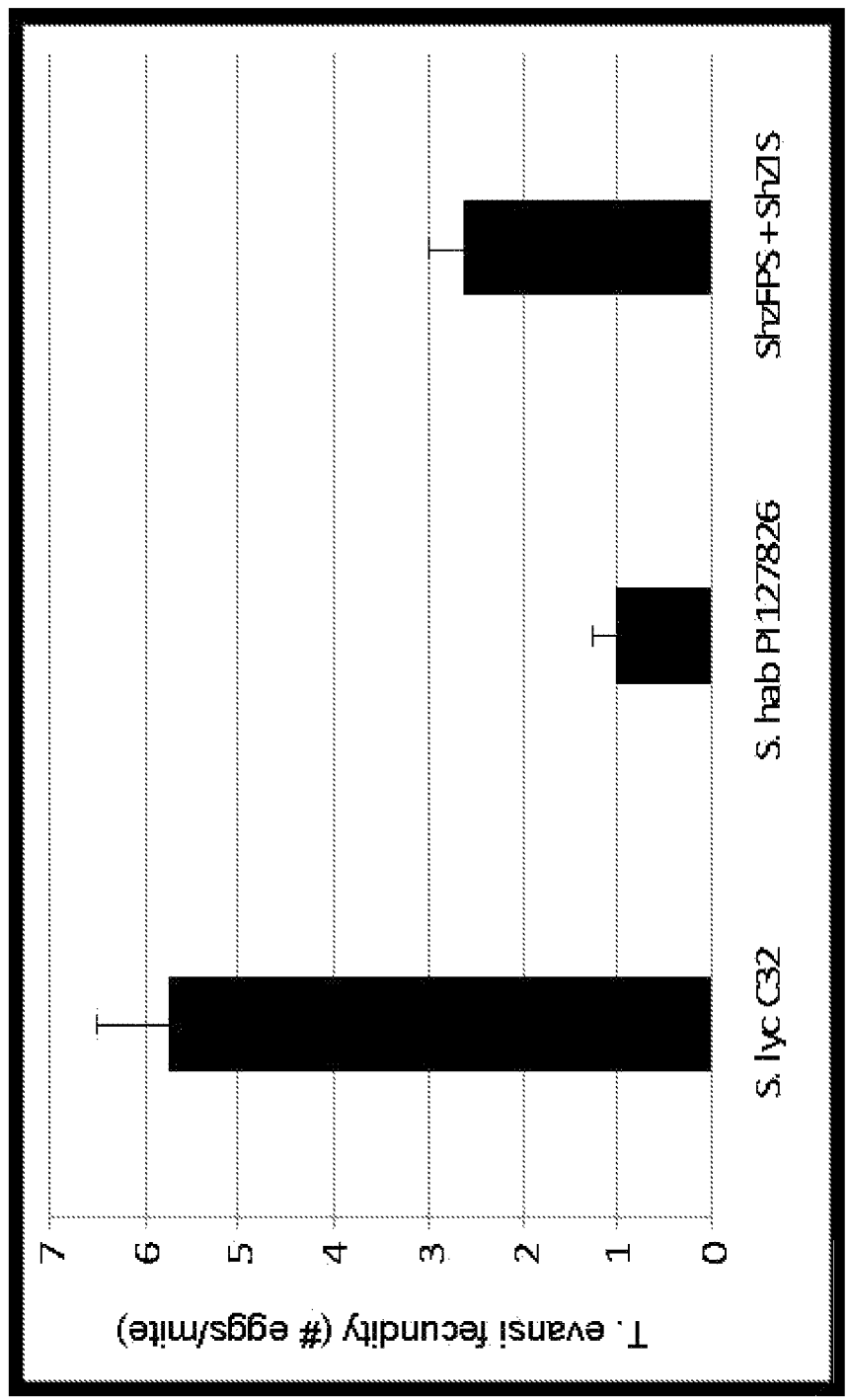

FIG. 11C displays Spider mite (*T. evansi*) fecundity on *S. lycopersicum* (C32), 7-epi-zingiberene producing transgenic *S. lycopersicum* (line 2) and *S. habrochaites* (PI127826).

Figure 11D:
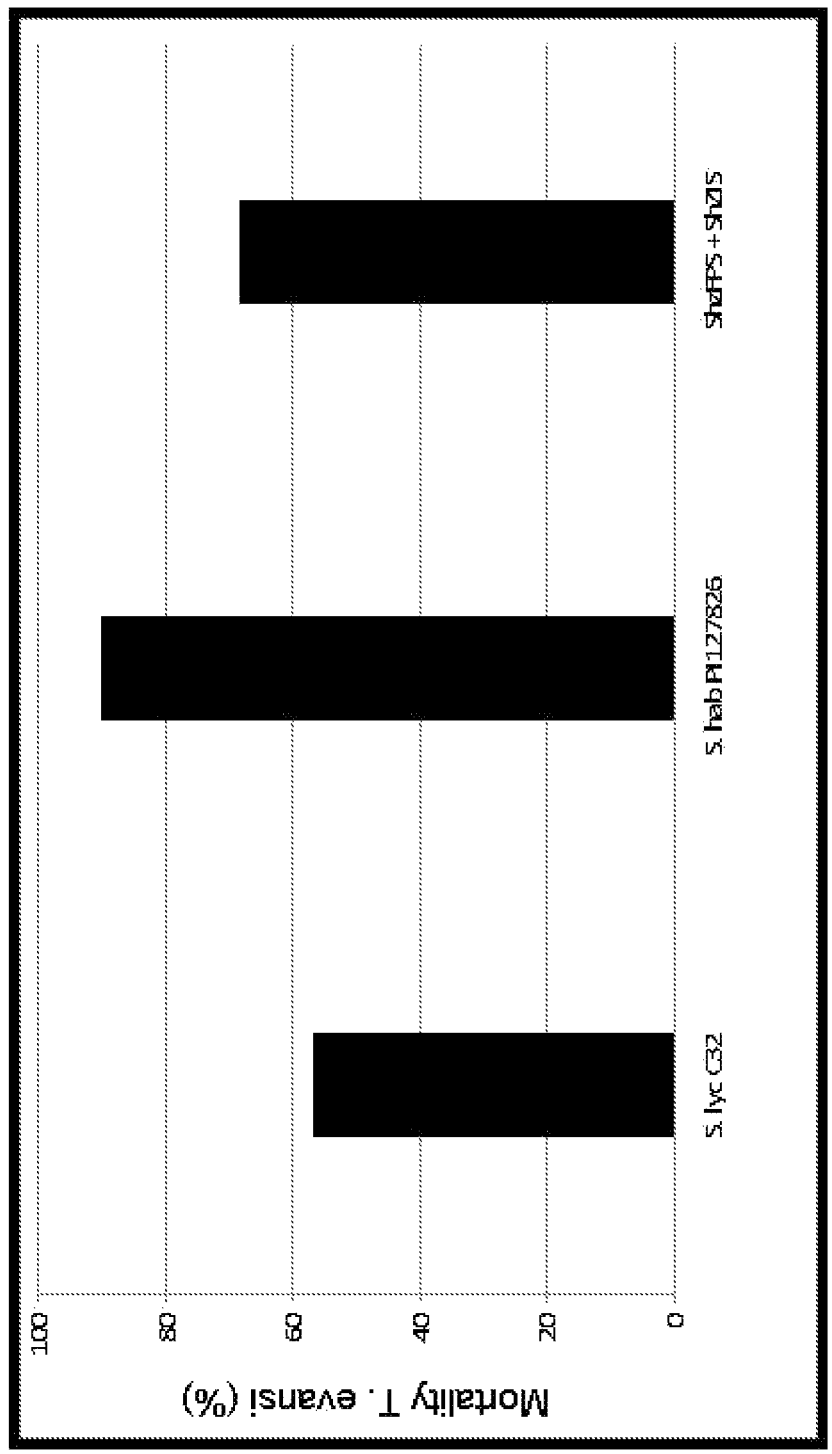

FIG. 11D demonstrates Spider mite (*T. evansi*) survival on *S. lycopersicum* (C32), 7-epi-zingiberene producing transgenic *S. lycopersicum* (line 2) and *S. habrochaites* (PI127826).

The following non-limiting Examples illustrate the different embodiments of the invention. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, and Sambrook and Russell (2001) *Molecular Cloning: A Laboratory*

*Manual*, Third Edition, Cold Spring Harbor Laboratory Press, NY; and in Volumes 1 and 2 of Ausubel et al. (1994) *Current Protocols in Molecular Biology, Current Protocols*, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK.

All references recited in the present disclosure are herein incorporated by reference.

EXAMPLES

Example 1

*E. coli* Expression Assay to Determine Production of 7-epizingiberene

Figure 2A:
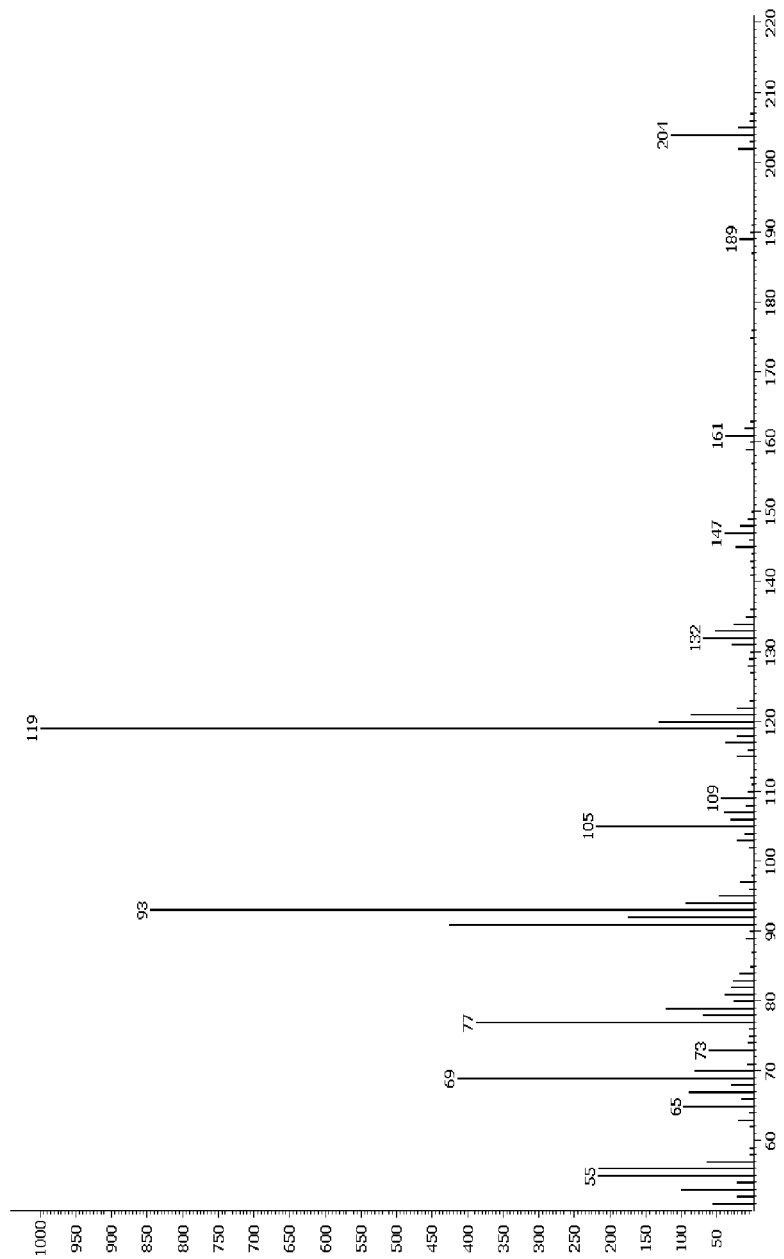
FIG. 2 shows mass spectra of 7-epizingiberene produced by expression of the nucleotide sequence encoding 7-epizingiberene synthase (FIG. 2A) in *E. coli* and 7-epizingiberene produced by *S. habrochaites* PI127826 trichomes (FIG. 2B).
Figure 2B:
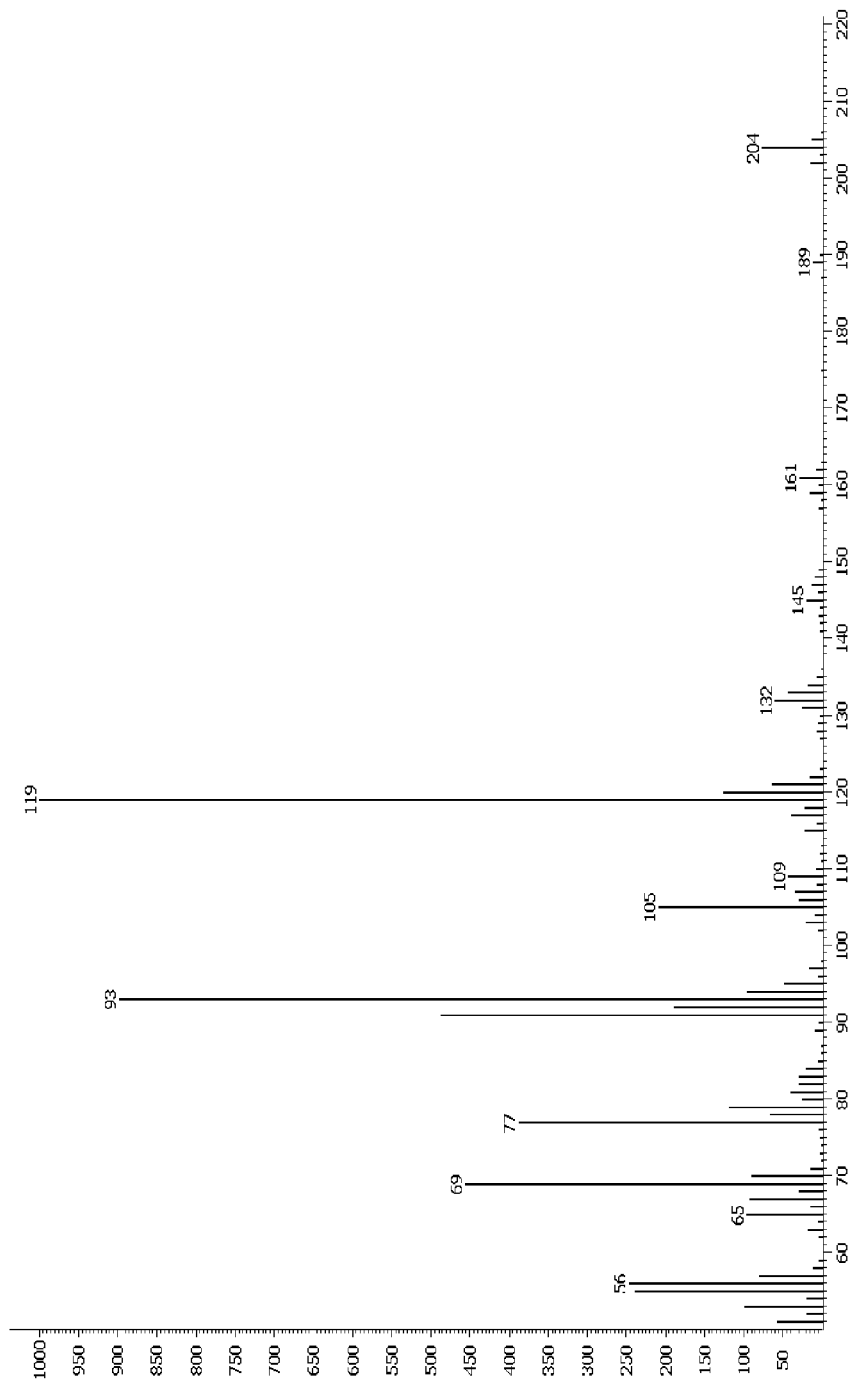

The full length gene (comprising SEQ ID NO:4 5' of SEQ ID NO:2 (SEQ ID NO:4-SEQ ID NO:2)) was cloned into the pGEX-KG expression vector (Guan and Dixon 1991). Constructs were transformed to C41 (DE3) *E. coli* cells (Dumon-Seignovert et al., 2004). As a control, empty pGEX-KG vector was transformed. A culture was grown to an $OD_{600}$ of 0.5-0.6 at 37° C. and placed at 4° C. for 30 min. Protein expression was induced with 1 mM isopropyl β-D-1-thiogalactopyranoside (IPTG). After 16 hours incubation at 16° C., cells were harvested by centrifugation. The supernatant was removed and the pellet was resuspended in assay buffer (25 mM HEPES, pH 7.2, 10 mM $MgCl_2$, 10% (v/v) glycerol) with added lysozyme (1 mg $mL^{-1}$) and proteinase inhibitors and incubated on ice for 30 minutes and subsequently sonicated. The lysate was centrifuged and the supernatant was stored at −80° C. Activity assays were performed in 500 μL 50 mM HEPES, pH7.2, 100 mM KCl, 7.5 mM $MgCl_2$, 20 μM $MgCl_2$, 5% (v/v) glycerol, 5 mM DTT with 50 μL protein and 2 mM cis-FPP (2Z-6Z-farnesyl diphosphate) as substrate. Enzyme products were analyzed by GC-MS with Solid Phase Micro Extraction fiber (SPME). Terpene products were identified using standards and comparing ion spectra, retention time and Kovats Index (see FIGS. 1 and 2).

Example 2

Determining the Enantiomer of Zingiberene Produced by the Various Genes/Proteins Activity assays were performed in 20 mL glass vials in a total volume of 500 μL 50 mM HEPES, pH7.2, 100 mM KCl, 7.5 mM $MgCl_2$, 20 μM $MgCl_2$, 5% (v/v) glycerol, 5 mM DTT with 50 μL protein and either 2 mM cis-FPP (2Z-6Z-farnesyl diphosphate), trans-FPP (E-E-farnesyl diphosphate), GPP (geranyl diphosphate), NDP (neryl diphosphate), or GGPP (geranylgeranyl diphosphate) as a substrate (Echelon Biosciences Incorporated, Salt Lake City, USA). Vials were closed with a teflon lined crimp cap immediately and incubated under moderate shaking for 1 hour at 30° C.

Enzyme products were sampled with a Solid Phase Micro Extraction fiber (SPME) for 10 minutes after the vial had been agitated and heated to 50° C. The fiber was desorbed for 1 minute in an Optic injector port (ATAS GL Int. Zoeterwoude, NL) which was kept at 220° C. For liquid injection 1-3 μL of sample in hexane was injected.

In order to separate alpha-zingiberene from 7-epizingiberene the Astec CHIRALDEX™ B-DM column (30 m×0.25 mm×0.12 μm film thickness; Supelco) was selected. The column was placed in an 6890 N gas chromatograph (Agilent, Amstelveen, NI). The programme was initially set to 115° C. for 3 minutes, increased to 140° C. by 4° C. $min^{-1}$ where it was kept for an additional minute after which the temperature slowly increased (2° C. $min^{-1}$) to 166° C. by where it was kept for 5 minutes prior to a rapid increase with 40° C. $min^{-1}$ to 220° C. Helium was used as a carrier gas. Mass spectra were generated with the ion source set to −70V at 200° C. and collected with a Time-of-Flight MS (Leco, Pegasus III, St. Joseph, Mich., USA) at 1850 V, with an acquisition rate of 20 scans per second.

Run time 1800 sec; Initial injector temperature: 220° C.; Final injector temperature: 220° C.; Transfer column flow: 1.5 mL $min^{-1}$; Transfer time: 120 sec; Initial column flow: 1 mL $min^{-1}$; Final column flow: 1 mL $min^{-1}$; Split flow: 25 mL $min^{-1}$ More columns specifics can be obtained via the supplier.

Results

Enantioselective gas chromatography on the cyclodextrin coated column allowed identification of the different zingiberene stereoisomers in *S. habrochaites* and ginger, previously inseparable by our GC-MS analysis. By NMR it was determined that *S. habrochaites* PI127826 produces 7-epizingiberene, whereas gingeroil contains alpha-zingiberene (Bleeker et al., 2011). Extracts from *S. habrochaites* and gingeroil were used as positive controls to study the enantiomer status of zingiberene synthesized by ObZIS (sweet lemon basil zingiberene synthase; Iijima et al., 2004) and ShZIS. Analysis (both liquid and SPME) indicated that the enzymes synthesize different stereoisomers. ShZIS is responsible for the production of 7-epizingiberene (similar to the enantiomer found in *S. habrochaites*), whereas ObZIS is a bona-fide alpha-zingiberene synthase (FIG. 3A,B).

FIG. 3A:

Liquid injection of samples in hexane. *S. habrochaites* leaf wash: standard for 7-epizingiberene (RT:844). Ginger oil: standard for alpha-zingiberene (RT: 851) and S-curcumene (RT:829). Mix leafwash and gingeroil: S-curcumene (RT: 829), 7 epizingiberene (RT:844) and alpha-zingiberene (RT: 851). Hexane overlay of *E. coli* C41 (DE3) transformed with pGEX:ZIS2 incubated with zFPP: 7-epizingiberene (RT: 844). This experiment shows separation of 7-epizingiberene and alpha-zingiberene (previously identified with NMR in Bleeker et al., 2011) on the chiral column and proves that heterologously expressed 7-epizingiberene synthase (ShZIS) is responsible for 7-epizingiberene in PI127826. It also shows that the F2 plant produces 7-epizingiberene.

FIG. 3B:

SPME: *S. habrochaites* leaf material as standard for 7-epizingiberene (RT: 850) and R-curcumene (RT:841). Gingeroil as standard for alpha-zingiberene (RT:856) and S-curcumene (RT:835). Sweet lemon basil ObZIS (Iijima, R. Davidovich-Rikanati, E. Fridman, D. R. Gang, E. Bar, E. Lewinsohn, and E. Pichersky (2004). The Biochemical and Molecular Basis for the Divergent Patterns in the Biosynthesis of Terpenes and Phenylpropenes in the Peltate Glands of Three Cultivars of Basil. Plant Physiology 136; 3724-3736) heterologously expressed and provided with E-E-FPP made alpha-zingiberene (RT:856). PI127826 ShZIS heterologously expressed and provided with Z-Z-FPP made 7-epizingiberene (RT:850). Mixed ObZIS and ShZIS showed both peaks. This experiments shows that ShZIS makes a different zingiberene stereoisomer than known plant zingiberene synthase ObZIS.

Example 3

Development of Transgenic *S. lycopersicum* Plants

Tomato Cotyledon Explant Transformation Experiments

Tomato (*S. lycopersicum*) line C32 was used for transformations with *Agrobacterium tumefaciens* (GV3101). The tomato transformation protocol has been described in Koornneef et al (1986) (Koornneef, Maarten, Jongsma, Maarten, Weide, Rob, Zabel, Pim, and Hille, Jacques. (1986); Transformation of tomato. In: Tomato Biotechnology, Donald Nevins and Richard Jones, eds. Alan Liss Inc., New York, USA, pg. 169-178) and in Koornneef et al (1987) (Koornneef, M., Hanhart, C. J., and Martinelli, L. (1987); A genetic analysis of cell culture traits in tomato. Theor. Appl. Genet. 74: 633-641). Trichome-specific targeting was ensured using MKS1 (methylketone synthase 1; Fridman et al., 2005 (Fridman E, Wang J, Iijima Y, Froehlich J E, Gang D R, Ohlrogge J, Pichersky E (2005). Metabolic, genomic, and biochemical analyses of glandular trichomes from the wild tomato species *Lycopersicon hirsutum* identify a key enzyme in the biosynthesis of methylketones. Plant Cell 17: 1252-1267)) and MTS1 (monoterpene synthase 1; WO2009082208) from *S. habrochaites* and *S. lycopersicum*, respectively. For co-transformation, *Agrobacterium* carrying a binary vector with pMKS1:zFPS and pMTS1:ShZIS were diluted cultures are mixed in a ratio of 1:1. The remainder of the described protocol has been unchanged. When tomato shoots appeared, they were harvested and rooted on solid MS20 medium containing 1 mg $L^{-1}$ IBA, 200 mg $L^{-1}$ cefotaxime, 200 mg $L^{-1}$ vancomycin, and 100 mg $L^{-1}$ kanamycin.

Genomic DNA was isolated from transgenic plants and PCR was performed on T0 plants to confirm successful insertion of the plasmids. Leaf material of T0 plants was harvested and analyzed by GC-MS as described above.

Results:

Bleeker et al. (2009) previously have shown that 7-epizingiberene is produced by *S. habrochaites* PI127826. The gene responsible for the production of 7-epizingiberene, called ShZIS, was isolated from *S. habrochaites* PI127826. Transgenic plants were produced by *Agrobacterium*-mediated transformation of *S. lycopersicum* C32. Whereas no 7-epizingiberene was formed in *S. lycopersicum* (C32) control plants or plants transformed with MKS1:zFPS only, 7-epizingiberene was present in transgenic *S. lycopersicum* plants with zFPS and ShZIS inserted into their genome (FIG. 4).

Example 5

Effect of the Expression of the 7-epizingiberene Synthase-encoding Nucleotide Sequence on Insect Pest Resistance Methodology Bioassays:

An interspecies cross between *S. lycopersicum* and *S. habrochaites* was performed and F2 lines were transferred to the greenhouse at the University of Amsterdam. The F2 plants were tested for their production of 7-epizingiberene. Cuttings were made of 7-epizingiberene producing F2 lines, *S. lycopersicum* C32 (moneymaker) and of *S. habrochaites* (PI127826). Both a parental line of the initial cross.

Bioassay *B. tabaci* (Whitefly)

Two cuttings of genotypes PI127826 and C32 and the respective F2s received 4 clip cages, each of which contained 20 adult *B. tabaci* (biotype Q) initially collected in Almeria (Spain) and reared continuously on cucumber under laboratory conditions (see Bleeker et al., 2009—Plant Physiol.). After 5 days, the total number and percentage of dead flies and total nr of eggs (combined abaxial and adaxial side of leaves) was determined.

In addition, leaf material of same leaflet was used to determine the terpene concentrations.

F2 plants have 7-epizingiberene levels comparable to *S. habrochaites* (PI127826). 7-epizingiberene was not detected in *S. lycopersicum* (C32).

Results Bioassay *B. tabaci*:

Cuttings of an F2 plant and *S. habrochaites* (PI127826) showed similar amounts of 7-epizingiberene. No 7-epizingiberene could be detected in *S. lycopersicum* C32 (FIG. 5). Moreover, increased resistance to whiteflies was observed in cuttings of the F2 plant and *S. habrochaites* (PI127826) (FIG. 6A,B). Compared to *S. habrochaites* and F2 plants, the percentage dead adults after 5 days was significantly lower on *S. lycopersicum* (FIG. 6A; One-way ANOVA, LSD; p<0.05 for both comparisons). Moreover, the number of eggs deposited by female *B. tabaci* adults was significantly higher on *S. lycopersicum* C32 compared to either F2 or *S. habrochaites* plants (FIG. 6B; One-way ANOVA, LSD; p<0.05 for both comparisons). Both the mortality and oviposition characteristics show that 7-epizingiberene produced by plants enhances resistance to whiteflies.

Bio-assay Colorado Potato Beetle (CPB)

Larvae of the CPB, *Leptinotarsa decemlineata* (order: Coleoptera) were reared on potato (cultivar Bintje). A no-choice assay with performed for 24 hours. CPB larvae (neonates) were allowed to feed on leaf discs (1.2 cm diameter) of F2 plants arisen from an interspecies cross between *S. lycopersicum* (C32) and *S. habrochaites* (PI127826).

F2 plant 40 shows high levels of zingiberene (similar to *S. habrochaites*), whereas F2 plant 45 only produced minute levels of zingiberene. Leaf discs from both genotypes were placed on wetted filter paper in a Petri dish and one larvae was allowed to feed for 24 hours (10 biological replicates per plant genotype). Subsequently, larvae survival and feeding damage were assessed.

Result Bio-assay CPB 7-epizingiberene levels were measured using the method described above. The F2 plant 40 shows high concentration of 7-epizingiberene, whereas F2 plant 45 produces only minute levels of 7-epizingiberene (concentration at the detection limit; FIG. 7A).

Larvael survival after 24 hours of feeding was significantly different on the two genotypes. Only 20% of the larvae survived on the high 7-epizingiberene producing F2-40 plant. In contrast, most larvae survived (70%) and were feeding from the low-producing plant (F2-45; FIG. 7B).

Feeding damage was assessed by scanning the leaf discs. Significantly more damage was observed on plants with low 7-epizingiberene (plant F2-45; FIG. 7C). Moreover, damage due to CPB feeding was quantified by using ImageJ. The analysis determines the number of pixels (arbitrary units) of scanned leaf discs. Damage was determined as the number of pixels for undamaged leaf discs compared to that of CPB damaged leaf discs. FIG. 7D indicates that significantly more damage was observed on leaf discs of plant F2-45, compared to F2-40 (high 7-epizingiberene production).

Bio-assay *Trialeurodes vaporariorum* (Greenhouse Whitefly)

*Trialeurodes vaporariorum* (order: Hemiptera) were reared on tomato (*S. lycopersicum*). A choice assay with performed for 24 hours. Adults were released in a cage with two F2 plants arisen from an interspecies cross between *S. lycopersicum* (C32) and *S. habrochaites* (PI127826). Subsequently, adult settling preference was determined on leaves of the following F2 plants (10 leaves per plant). F2 plant 40 showed high levels of 7-epizingiberene (similar to *S. habrochaites*), whereas F2 plant 45 only produced minute levels of 7-epi-zingiberene (FIG. 7A).

Results Bio-assay *Trialeurodes vaporariorum*

Greenhouse whitefly preference was different on the two genotypes (FIG. 8). Compared to the high 7-epizingiberene producing plants (F2-40), twice as many greenhouse whitefly adults settled on the low 7-epizingiberene producing plants (F2-45).

Bio-assay *Macrosiphum euphorbiae* (Potato/Tomato Aphid)

*Macrosiphum euphorbiae* (order: Hemiptera) were reared on tomato (*S. lycopersicum*). A no-choice assay was performed for 48 hours. One adult aphid was placed in a clip-cage on either of two F2 plants arisen from an interspecies cross between *S. lycopersicum* (C32) and *S. habrochaites* (PI127826). Subsequently, aphid performance (survival and number of offspring) was determined on the following F2 plants (3 clip-cages per plant; 6 plants per genotype). F2 plant 40 shows high levels of 7-epizingiberene (similar to *S. habrochaites*), whereas F2 plant 45 only produced minute levels of 7-epizingiberene (FIG. 7A).

Results Bio-assay *Macrosiphum euphorbiae*

Aphid performance was different on the two genotypes (FIG. 9). Compared to the high 7-epizingiberene producing plants (F2-40), aphids performed better in terms of survival and number of offspring produced on low 7-epizingiberene producing plants (F2-45).

Bio-assay *Tuta absoluta*

*Tuta absoluta* (order: Lepidoptera) were reared on tomato (*S. lycopersicum*). A no-choice assay was performed for 7 days. 5 adults were allowed to oviposit their eggs on *S. lycopersicum* (C32) plants and on F2 plants arisen from an interspecies cross between *S. lycopersicum* (C32) and *S. habrochaites* (PI127826). After 7 days, *Tuta abosoluta* oviposition (number of eggs deposited) was determined on the abaxial and adaxial side of six leaves per plant genotype. F2 plants were characterized for 7-epizingiberene content after the assay and *Tuta abosoluta* oviposition (number of eggs deposited) was correlated to the content of 7-epizingiberene.

Results Bio-assay *Tuta absoluta*

Oviposition by *Tuta absoluta* females was significantly reduced on F2 plants producing 7-epizingiberene (FIG. 10*a*). FIG. 10*b* indicates the 7-epizingiberene concentration in the F2 plants tested for *Tuta absoluta* ovipostition. Oviposition was negatively correlated with 7-epizingiberene content (combination of FIGS. 10A and 10B).

Bio-assay Spider Mites

Spider mites, like insects, belong to the arthropods but are a different class of organisms. The effect of 7-epizingiberene was tested on two spider mite species, *Tetranychus urticae* and *T. evansi*. Both arthropod species were reared on common garden bean. A 4-day no-choice assay was performed with synchronized populations of *T. urticae* and *T. evansi*. Mites were place on leaf discs of susceptible control plants (*S. lycopersicum*), resistant *S. habrochaites* PI127826 plants and on 7-epizingiberene producing transgenic *S. lycopersicum* plants (line 2). Subsequently, mite survival and fecundity (number of eggs/mite) was assessed. Transgenic plants were made as described above. In short, plants were co-transformed with two constructs to produce 7-epizingiberene in glandular trichomes of *S. lycopersicum* (pMKS1:zFPS and pMTS1:ShZIS). In this experiment one transgenic line was used (line 2).

Results Bio-assay Spider Mites

Mite fecundity was reduced by the production of 7-epizingiberene in transgenic *S. lycopersicum* plants. Compared to *S. lycopersicum*, transgenic plants that produced 7-epizingiberene showed reduced mite survival (both species). Moreover, FIGS. 11A and 11C indicate a strong reduction of mite fecundity (eggs/mite) for both *T. urticae* and *T. evansi*, 81% and 54% reduction, respectively.

Overall survival was also impacted for both spider mite species. FIGS. 11B and 11D indicate that the percentage of dead spider mites was higher on transgenic plants producing 7-epizingiberene compared to non-7-epizingiberene-producing *S. lycopersicum* plants (*S. lyc* 32).

Example 5

7-epi-zingiberene Production in Various Plants

*Arabidopsis thaliana, Nicotiana tabacum, Cucumis melo, Lactuca sativa, Glycine max*, and *Gossypium hirsutum* are co-transformed with ShzFPS (additional zFPP precursor) and ShZIS (encoding 7-epizingiberene synthase). 7-epi-zingiberene production in the leaves of co-transformed plants is compared to 7-epi-zingiberene production in mock-transformed plants of the same species. *Arabidopsis thaliana, Nicotiana tabacum, Cucumis melo, Lactuca sativa, Glycine max*, and *Gossypium hirsutum* are capable of producing 7-epi-zingiberene.

The invention claimed is:

1. A method for preparing 7-epizingiberene and/or R-curcumene comprising:
   a) transforming a host cell with a recombinant nucleic acid molecule comprising a nucleic acid sequence encoding a polypeptide comprising the amino acid sequence of SEQ ID NO: 1 or an amino acid sequence at least 99% identical to the full length of SEQ ID NO: 1, wherein in the transformed host cell the nucleic acid sequence encoding the polypeptide is operably linked to an active promoter; and
   b) culturing said host cell under conditions permitting production of 7-epizingiberene and/or R-curcumene.

2. A method for producing 7-epizingiberene from zFPP in a host cell, comprising:
   a) introducing into said host cell a first nucleic acid sequence encoding a polypeptide comprising the amino acid sequence of SEQ ID NO:6 or an amino acid sequence at least 95% identical to the full length of SEQ ID NO:6 over the entire length, and a second nucleic acid sequence encoding a polypeptide comprising the amino acid sequence of SEQ ID NO: 1 or an amino acid sequence at least 99% identical to the full length of SEQ ID NO:1, wherein in the host cell obtained then first nucleic acid sequence and second nucleic acid sequence are operably linked to an active promoter;
   b) culturing the host cell in suitable conditions for the expression of said first and said second nucleic acid sequences; and,
   c) collecting the 7-epizingiberene contained in said cell and/or in a culture medium thereof.

3. A method for producing a transgenic plant having enhanced insect pest resistance compared to a non-transgenic control plant, said method comprising the steps of:
   (a) transforming a plant or plant cell with a nucleic acid molecule encoding a polypeptide comprising the amino acid sequence of SEQ ID NO: 1 or an amino acid sequence at least 99% identical to the full length of SEQ ID NO:1, operably linked to a promoter active in plant cells; and
   (b) regenerating a plant.

4. The method according to claim 3, wherein said nucleic acid molecule is integrated into the genome of said plant.

5. The method according to claim 3, further comprising the step of
(c) creening the regenerated plant, or a plant derived therefrom by selfing or crossing, for resistance to one or more insect pests and identifying a plant comprising enhanced resistance to one or more of said insect pests.

6. The method according to claim 3, wherein said promoter is an insect pest inducible promoter.

7. The method according to claim 3, wherein the plant belongs to the family Solanaceae.

8. The method according to claim 7, wherein the plant is of the genus *Solanum*.

9. The method according to claim 3, wherein the method further comprises the step of:
transforming the plant or plant cell with a nucleic acid molecule encoding the amino acid sequence of SEQ ID NO:6 or an amino acid sequence comprising at least 80% amino acid sequence identity to the amino acid sequence of SEQ ID NO:6, over the entire length, operably linked to a promoter active in plant cells.

10. The method according to claim 1, further comprising the step of c) isolating the 7-epizingiberene produced in step b).

11. The method according to claim 10, further comprising the steps of d) dehydrogenating the 7-epizingiberene to produce R-curcumene.

12. The method according to claim 1, wherein the nucleic acid sequence is operably linked to a heterologous promoter in the transformed host cell.

13. The method according to claim 1, wherein the nucleic acid sequence encodes a polypeptide comprising the amino acid sequence of SEQ ID NO: 1.

14. The method according to claim 1, wherein the recombinant nucleic acid molecule comprises a cDNA sequence that encodes a polypeptide comprising the amino acid sequence of SEQ ID NO: 1 or an amino acid sequence at least 99% identical to the full length of SEQ ID NO:1.

15. The method according to claim 2, wherein the second nucleic acid sequence is operably linked to a heterologous promoter in the transformed host cell.

16. The method according to claim 2, wherein the first nucleic acid sequence encodes a polypeptide comprising the amino acid sequence of SEQ ID NO: 6, and the second nucleic acid sequence encodes a polypeptide comprising the amino acid sequence of SEQ ID NO: 1.

17. The method according to claim 2, wherein the second nucleic acid sequence comprises a cDNA sequence that encodes a polypeptide comprising the amino acid sequence of SEQ ID NO: 1 or an amino acid sequence at least 99% identical to the full length of SEQ ID NO:1.

18. A method for preparing 7-epizingiberene and/or R-curcumene comprising the steps of: a) culturing a host cell transformed with a recombinant nucleic acid molecule comprising a nucleic acid sequence that encodes a polypeptide comprising the amino acid sequence of SEQ ID NO: 1 or an amino acid sequence at least 99% identical to the full length of SEQ ID NO: 1, wherein in the host cell the nucleic acid sequence encoding the polypeptide is operably linked to an active promoter, under conditions permitting production of 7-epizingiberene and/or R-curcumene.

19. The method according to claim 18, further comprising the step of b) isolating the 7-epizingiberene produced in step a).

20. The method according to claim 19, further comprising the steps of c) dehydrogenating the 7-epizingiberene to produce R-curcumene.

21. A method for preparing 7-epizingiberene and/or R-curcumene comprising the steps of:
a) heterologously expressing in a host cell a polypeptide comprising the amino acid sequence of SEQ ID NO: 1 or an amino acid sequence at least 99% identical to the full length of SEQ ID NO: 1, under conditions permitting production of 7-epizingiberene.

22. The method according to claim 21, further comprising the step of b) isolating the 7-epizingiberene produced in step a).

23. The method according to claim 22, further comprising the steps of c) dehydrogenating the 7-epizingiberene to produce R-curcumene.

* * * * *

UNITED STATES PATENT AND TRADEMARK OFFICE
CERTIFICATE OF CORRECTION

| | | |
|---|---|---|
| PATENT NO. | : 9,234,193 B2 | Page 1 of 1 |
| APPLICATION NO. | : 14/122579 | |
| DATED | : January 12, 2016 | |
| INVENTOR(S) | : Robert Cornelis Schuurink et al. | |

It is certified that error appears in the above-identified patent and that said Letters Patent is hereby corrected as shown below:

IN THE CLAIMS:

Claim 5, line 3, column 45: "(c) creening the regenerated plant…" should read -- (c) screening the regenerated plant… --

Claim 7, line 10, column 45: "Solanaceae" should read -- *Solanaceae* --

Signed and Sealed this
Third Day of May, 2016

Michelle K. Lee
*Director of the United States Patent and Trademark Office*

SEQUENCE LISTING

```
<160> NUMBER OF SEQ ID NOS: 8

<210> SEQ ID NO 1
<211> LENGTH: 741
<212> TYPE: PRT
<213> ORGANISM: Solanum habrochaites

<400> SEQUENCE: 1

Cys Ser His Ser Thr Pro Ser Ser Met Asn Gly Phe Glu Asp Ala Arg
1               5                   10                  15

Asp Arg Ile Arg Glu Ser Phe Gly Lys Val Glu Leu Ser Pro Ser Ser
            20                  25                  30

Tyr Asp Thr Ala Trp Val Ala Met Val Pro Ser Lys His Ser Leu Asn
        35                  40                  45
```

```
Glu Pro Cys Phe Pro Gln Cys Leu Asp Trp Ile Ile Glu Asn Gln Arg
 50                  55                  60

Glu Asp Gly Ser Trp Gly Leu Asn Pro Ser His Pro Leu Leu Leu Lys
 65                  70                  75                  80

Asp Ser Leu Ser Ser Thr Leu Ala Cys Leu Leu Ala Leu Thr Lys Trp
                 85                  90                  95

Arg Val Gly Asp Glu Gln Ile Lys Arg Gly Leu Gly Phe Ile Glu Thr
            100                 105                 110

Gln Ser Trp Ala Ile Asp Asn Lys Asp Gln Ile Ser Pro Leu Gly Phe
        115                 120                 125

Glu Ile Ile Phe Pro Ser Met Ile Lys Ser Ala Glu Lys Leu Asn Leu
130                 135                 140

Asn Leu Ala Ile Asn Lys Arg Asp Ser Thr Ile Lys Arg Ala Leu Gln
145                 150                 155                 160

Asn Glu Phe Thr Arg Asn Ile Glu Tyr Met Ser Gly Phe Gly Glu
            165                 170                 175

Leu Cys Asp Trp Lys Glu Ile Ile Lys Leu His Gln Arg Gln Asn Gly
            180                 185                 190

Ser Leu Phe Asp Ser Pro Ala Thr Thr Ala Ala Leu Ile Tyr His
        195                 200                 205

Gln His Asp Lys Lys Cys Tyr Glu Tyr Leu Asn Ser Ile Leu Gln Gln
210                 215                 220

His Lys Asn Trp Val Pro Thr Met Tyr Pro Thr Lys Ile His Ser Leu
225                 230                 235                 240

Leu Cys Leu Val Asp Thr Leu Gln Asn Leu Gly Val His Arg His Phe
                245                 250                 255

Lys Ser Glu Ile Lys Lys Ala Leu Asp Glu Ile Tyr Arg Leu Trp Gln
            260                 265                 270

Gln Lys Asn Glu Glu Ile Phe Ser Asn Val Thr His Cys Ala Met Ala
        275                 280                 285

Phe Arg Leu Leu Arg Ile Ser Tyr Tyr Asp Val Ser Ser Asp Glu Leu
290                 295                 300

Ala Glu Phe Val Asp Glu Glu His Phe Phe Ala Thr Ser Gly Lys Tyr
305                 310                 315                 320

Thr Ser His Val Glu Ile Leu Glu Leu His Lys Ala Ser Gln Leu Ala
                325                 330                 335

Ile Asp His Glu Lys Asp Asp Ile Leu Asp Lys Ile Asn Asn Trp Thr
            340                 345                 350

Arg Thr Phe Met Glu Gln Lys Leu Leu Asn Asn Gly Phe Ile Asp Arg
        355                 360                 365

Met Ser Lys Lys Glu Val Glu Leu Ala Leu Arg Asn Phe Tyr Ile Ile
370                 375                 380

Ser Asp Leu Ala Glu Asn Arg Arg Tyr Ile Lys Ser Tyr Glu Glu Asn
385                 390                 395                 400

Asn Phe Lys Ile Leu Lys Ala Ala Tyr Arg Ser Pro Asn Ile Asn Asn
                405                 410                 415

Lys Asp Leu Phe Ile Phe Ser Ile Arg Asp Phe Glu Leu Cys Gln Ala
            420                 425                 430

Gln His Gln Glu Glu Leu Gln Leu Lys Arg Trp Phe Glu Asp Cys
        435                 440                 445

Arg Leu Asp Gln Leu Gly Leu Ser Glu Gln Phe Ile Ser Ala Ser Tyr
450                 455                 460

Leu Cys Ala Ile Pro Ile Val Pro Gly Pro Glu Leu Ser Asp Ala Arg
```

-continued

```
                 465                 470                 475                 480
             Leu Val Tyr Ala Lys Tyr Val Met Leu Leu Thr Ile Val Asp Asp His
                             485                 490                 495

Phe Glu Ser Phe Ala Ser Thr Asp Glu Cys Leu Asn Ile Ile Glu Leu
                             500                 505                 510

Val Glu Arg Trp Asp Asp Tyr Ala Ser Val Gly Tyr Lys Ser Glu Arg
                             515                 520                 525

Val Lys Val Leu Phe Ser Met Phe Tyr Lys Ser Ile Glu Glu Ile Ala
                             530                 535                 540

Thr Ile Ala Glu Ile Lys Gln Gly Arg Ser Val Lys Asn His Leu Ile
             545                 550                 555                 560

Asn Leu Trp Leu Lys Val Met Lys Leu Met Leu Met Glu Arg Val Glu
                             565                 570                 575

Trp Cys Ser Gly Lys Thr Ile Pro Arg Ile Glu Glu Tyr Leu Tyr Val
                             580                 585                 590

Ser Ser Ile Thr Phe Gly Ser Arg Leu Ile Pro Leu Thr Thr Gln Tyr
                             595                 600                 605

Phe Ile Gly Ile Lys Ile Ser Lys Asp Leu Leu Glu Ser Asp Glu Ile
                             610                 615                 620

Tyr Gly Leu Cys Asn Phe Thr Gly Ile Val Leu Arg Leu Leu Asn Asp
             625                 630                 635                 640

Leu Gln Asp Ser Lys Arg Glu Gln Lys Glu Gly Ser Ile Asn Leu Val
                             645                 650                 655

Thr Leu Leu Met Lys Ser Ile Ser Glu Glu Ala Ile Met Lys Met
                             660                 665                 670

Lys Glu Ile Leu Glu Met Lys Arg Arg Glu Leu Phe Lys Met Val Leu
                             675                 680                 685

Val Gln Lys Lys Gly Ser Gln Leu Pro Gln Leu Cys Lys Glu Ile Phe
                             690                 695                 700

Trp Arg Thr Cys Lys Trp Ala His Phe Thr Tyr Ser Gln Thr Asp Arg
             705                 710                 715                 720

Tyr Arg Phe Pro Glu Glu Met Glu Asn His Ile Asp Glu Val Phe Tyr
                             725                 730                 735

Lys Pro Leu Asn His
                             740

<210> SEQ ID NO 2
<211> LENGTH: 2226
<212> TYPE: DNA
<213> ORGANISM: Solanum habrochaites

<400> SEQUENCE: 2
tgcagccaca gtacccttc atcaatgaat ggtttcgaag atgcaaggga tagaataagg     60
gaaagttttg ggaaagtaga gttatctcct tcttcctatg acacagcatg ggtagctatg    120
gtcccttcaa acattcact aaatgagcca tgttttccac aatgtttgga ttggattatt    180
gaaaatcaaa gagaagatgg atcttgggga ctaaaccta gccatccatt gcttcttaag    240
gactcacttt cttccactct tgcatgtttg cttgcactaa ccaaatggag agttggagat    300
gagcaaatca aagaggcct tggctttatt gaaacccaga gttgggcaat tgataacaag    360
gatcaaattt cacctctagg atttgaaatt atatttccca gtatgatcaa gtctgcagaa    420
aaactaaact taaatctagc aattaacaaa agagattcaa cattaaaag agcattacag    480 aatgagttca cgaggaatat tgaatatatg agtgaaggat ttggtgaatt atgtgattgg    540
```

| aaggaaataa taaagttaca tcaaaggcaa aatggttcat tatttgattc accagccact | 600 |
| actgcagctg ccttgattta ccatcagcat gataaaaaat gctatgaata tcttaattca | 660 |
| atcttgcaac aacacaaaaa ttgggttccc actatgtatc caacaaagat acattcattg | 720 |
| ctttgcttgg ttgatacact tcaaaatctt ggagtacatc ggcattttaa atcagaaata | 780 |
| aagaaagccc tagatgaaat atacaggcta tggcaacaaa agaatgaaga aatttttctca | 840 |
| aatgtcaccc attgtgctat ggcttttcga cttctaagga taagctacta tgatgtctcc | 900 |
| tcagatgaac tagcagaatt tgtggatgaa gaacatttct ttgcaacaag tgggaaatat | 960 |
| acaagtcatg ttgaaattct tgaactccac aaagcatcac aattggctat tgatcatgag | 1020 |
| aaagatgaca ttttggataa gattaacaat tggacaagaa catttatgga gcaaaaactc | 1080 |
| ttaaacaatg gcttcataga taggatgtca aaaaaggagg tggaacttgc tttgaggaat | 1140 |
| ttttatatca tatctgatct agcagaaaat agaagatata taaagtcata cgaagagaac | 1200 |
| aattttaaaa tcttaaaagc agcttatagg tcacctaaca ttaacaataa ggacttgttt | 1260 |
| atattttcaa tacgcgactt tgaattatgc caagctcaac accaagaaga acttcaacaa | 1320 |
| ctcaagaggt ggtttgaaga ttgtagattg gaccaactcg gactttcgga acaatttata | 1380 |
| tctgctagtt acttatgtgc tattcctatt gtccccgggc tgaattatc cgatgctcgt | 1440 |
| ctcgtgtacg cgaaatacgt catgctcttg actattgtcg atgatcattt cgagagtttt | 1500 |
| gcatctacag atgaatgtct caacatcatt gaattagtag aaaggtggga tgactatgca | 1560 |
| agtgtaggtt ataaatctga gagggttaaa gttttattt caatgtttta caatcaata | 1620 |
| gaggagattg caacaattgc tgaaattaaa caaggacgat ctgtcaaaaa tcaccttatt | 1680 |
| aatttgtggc ttaaagtgat gaagttgatg ttgatggaac gagtagagtg gtgttctggc | 1740 |
| aagacaatac caagaataga agagtatttg tatgttagtt ctataacatt tggttcaaga | 1800 |
| ttgattcctc tcacaacaca atattttatt ggaataaaaa tatccaaaga tcttttagaa | 1860 |
| agtgatgaaa tttatggttt atgcaatttt accggtatag tcttgaggct cctcaatgat | 1920 |
| ttacaagatt ccaagagaga acaaaaggag ggctcaataa atttagtcac attactaatg | 1980 |
| aaaagtatct ctgaggaaga agctataatg aagatgaagg aaatcttgga atgaaaaga | 2040 |
| agagagttat ttaaaatggt tttagttcaa aaaaagggaa gccaattgcc tcaattatgc | 2100 |
| aaagaaatat tttggaggac atgcaaatgg gctcatttca cttattcaca aactgataga | 2160 |
| tatagatttc cagaggaaat ggagaatcac attgatgaag tcttttacaa accactcaat | 2220 |
| cattaa | 2226 |

<210> SEQ ID NO 3
<211> LENGTH: 36
<212> TYPE: PRT
<213> ORGANISM: Solanum habrochaites

<400> SEQUENCE: 3

Met Ile Val Gly Tyr Arg Ser Thr Ile Ile Thr Leu Ser His Pro Lys
1               5                   10                  15
Leu Gly Asn Gly Lys Thr Ile Ser Ser Asn Ala Ile Phe Arg Arg Ser
            20                  25                  30
Cys Arg Val Arg
        35

<210> SEQ ID NO 4
<211> LENGTH: 108
<212> TYPE: DNA

<213> ORGANISM: Solanum habrochaites

<400> SEQUENCE: 4

```
atgatagttg gctatagaag cacaatcata acccttttctc atcctaagct aggcaatggg    60
aaaacaattt catccaatgc aattttccgg agatcatgta gagtaaga                108
```

<210> SEQ ID NO 5
<211> LENGTH: 777
<212> TYPE: DNA
<213> ORGANISM: Solanum habrochaites

<400> SEQUENCE: 5

```
gctcgtggac tcaacaagat ttcatgctca ctcagcttac aaaccgaaaa actttgttat    60
gaggataatg ataatgatct tgatgaagaa cttatgccta acacattgc tttgataatg    120 gatggtaata ggagatgggc aaaggataag ggtttagacg tatccgaagg tcacaaacat    180
ctctttccaa aattaaaaga gatttgtgac atttcttcta aattgggaat acaagttatc    240
actgcttttg cattctctac tgaaaattgg aaacgagcca aggggaggt tgatttcttg    300 atgcaaatgt tcgaagaact ctatgatgag ttttcgaggt ctggagtaag agtgtctatt    360
attggttgta aaaccgacct cccaatgaca ttacaaaaat gcatagcatt aacagaagag    420
actacaaagg gaaacaaagg acttcacctt gtgattgcac taaactatgg tggatattat    480
gacatattgc aagcaacaaa aagcattgtt aataaagcaa tgaatggttt attagatgta    540
gaaaatatca acaagaattt atttgatcaa gaacttgaaa gcaagtgtcc aaatcctgat    600
ttacttataa ggacaggagg tgttcaaaga gttagtaact ttttgttgtg caattggct    660 tatactgaat ttacttcac caaaacattg tttcctgatt ttggagagga agatcttaaa    720
gaggcaataa taaactttca acaaaggcat agacgttttg gtggacacac atattga      777
```

<210> SEQ ID NO 6
<211> LENGTH: 258
<212> TYPE: PRT
<213> ORGANISM: Solanum habrochaites

<400> SEQUENCE: 6

```
Ala Arg Gly Leu Asn Lys Ile Ser Cys Ser Leu Ser Leu Gln Thr Glu
1               5                   10                  15

Lys Leu Cys Tyr Glu Asp Asn Asp Asn Asp Leu Asp Glu Glu Leu Met
            20                  25                  30

Pro Lys His Ile Ala Leu Ile Met Asp Gly Asn Arg Arg Trp Ala Lys
        35                  40                  45

Asp Lys Gly Leu Asp Val Ser Glu Gly His Lys His Leu Phe Pro Lys
    50                  55                  60

Leu Lys Glu Ile Cys Asp Ile Ser Ser Lys Leu Gly Ile Gln Val Ile
65                  70                  75                  80

Thr Ala Phe Ala Phe Ser Thr Glu Asn Trp Lys Arg Ala Lys Gly Glu
                85                  90                  95

Val Asp Phe Leu Met Gln Met Phe Glu Glu Leu Tyr Asp Glu Phe Ser
            100                 105                 110

Arg Ser Gly Val Arg Val Ser Ile Ile Gly Cys Lys Thr Asp Leu Pro
        115                 120                 125

Met Thr Leu Gln Lys Cys Ile Ala Leu Thr Glu Glu Thr Thr Lys Gly
    130                 135                 140

Asn Lys Gly Leu His Leu Val Ile Ala Leu Asn Tyr Gly Gly Tyr Tyr
145                 150                 155                 160
```

```
Asp Ile Leu Gln Ala Thr Lys Ser Ile Val Asn Lys Ala Met Asn Gly
                165                 170                 175

Leu Leu Asp Val Glu Asn Ile Asn Lys Asn Leu Phe Asp Gln Glu Leu
            180                 185                 190

Glu Ser Lys Cys Pro Asn Pro Asp Leu Leu Ile Arg Thr Gly Gly Val
        195                 200                 205

Gln Arg Val Ser Asn Phe Leu Leu Trp Gln Leu Ala Tyr Thr Glu Phe
    210                 215                 220

Tyr Phe Thr Lys Thr Leu Phe Pro Asp Phe Gly Glu Glu Asp Leu Lys
225                 230                 235                 240

Glu Ala Ile Ile Asn Phe Gln Gln Arg His Arg Arg Phe Gly Gly His
                245                 250                 255

Thr Tyr

<210> SEQ ID NO 7
<211> LENGTH: 45
<212> TYPE: PRT
<213> ORGANISM: Solanum habrochaites

<400> SEQUENCE: 7

Met Ser Ser Leu Val Leu Gln Cys Trp Lys Leu Ser Ser Pro Ser Leu
1               5                   10                  15

Ile Leu Gln Gln Asn Thr Ser Ile Ser Met Gly Ala Phe Lys Gly Ile
            20                  25                  30

His Lys Leu Gln Ile Pro Asn Ser Pro Leu Thr Val Ser
        35                  40                  45

<210> SEQ ID NO 8
<211> LENGTH: 135
<212> TYPE: DNA
<213> ORGANISM: Solanum habrochaites

<400> SEQUENCE: 8
atgagttctt tggttcttca atgttggaaa ttatcatctc catctctgat tttacaacaa      60
aatacatcaa tatccatggg tgcattcaaa ggtattcata aacttcaaat cccaaattca     120
cctctgacag tgtct                                                      135
```